United States Patent
Andrews et al.

(10) Patent No.: US 11,292,799 B2
(45) Date of Patent: Apr. 5, 2022

(54) SUBSTITUTED AZETIDINE DIHYDROTHIENOPYRIMIDINES AND THEIR USE AS PHOSPHODIESTERASE INHIBITORS

(71) Applicant: UNION therapeutics A/S, Hellerup (DK)

(72) Inventors: Mark Andrews, Ballerup (DK); Daniel Rodriguez Greve, Ballerup (DK); Jens Larsen, Ballerup (DK)

(73) Assignee: UNION THERAPEUTICS A/S, Hellerup (DK)

( * ) Notice: Subject to any disclaimer, the term of this patent is extended or adjusted under 35 U.S.C. 154(b) by 101 days.

(21) Appl. No.: 16/772,428

(22) PCT Filed: Dec. 14, 2018

(86) PCT No.: PCT/EP2018/084974
§ 371 (c)(1),
(2) Date: Jun. 12, 2020

(87) PCT Pub. No.: WO2019/115774
PCT Pub. Date: Jun. 20, 2019

(65) Prior Publication Data
US 2021/0070769 A1 Mar. 11, 2021

(30) Foreign Application Priority Data
Dec. 15, 2017 (EP) ..................................... 17207659

(51) Int. Cl.
*C07D 495/04* (2006.01)
(52) U.S. Cl.
CPC .................................. *C07D 495/04* (2013.01)
(58) Field of Classification Search
CPC ........ C07D 495/04; A61K 45/06; A61P 17/00
See application file for complete search history.

(56) References Cited

U.S. PATENT DOCUMENTS

| | | | |
|---|---|---|---|
| 7,511,045 B2 | 3/2009 | Hoenke et al. | |
| 8,114,878 B2 | 2/2012 | Pouzet et al. | |
| 8,486,948 B2 | 7/2013 | Pouzet et al. | |
| 8,637,519 B2 | 1/2014 | Pouzet et al. | |
| 8,754,073 B2 | 6/2014 | Pouzet et al. | |
| 9,161,927 B2 | 10/2015 | Nickolaus et al. | |
| 2007/0259846 A1 | 11/2007 | Hoenke et al. | |
| 2011/0028441 A1* | 2/2011 | Pouzet | A61P 11/06 514/171 |
| 2013/0225609 A1* | 8/2013 | Nickolaus | A61K 31/519 514/260.1 |

FOREIGN PATENT DOCUMENTS

| | | |
|---|---|---|
| CA | 2605161 | 10/2006 |
| CA | 2647243 | 10/2007 |
| CA | 2702447 | 4/2009 |
| CA | 2702518 | 4/2009 |
| CA | 2702524 | 4/2009 |
| CA | 2705414 | 4/2009 |
| CA | 2753604 | 9/2010 |
| WO | WO 2006/111549 | 10/2006 |
| WO | WO 2007/118793 | 10/2007 |
| WO | WO 2009/050236 | 4/2009 |
| WO | WO 2009/050242 | 4/2009 |
| WO | WO 2009/050248 | 4/2009 |
| WO | WO 2009/053268 | 4/2009 |
| WO | WO 2010/097334 | 9/2010 |
| WO | WO 2011/124525 | 10/2011 |
| WO | WO 2013/026797 | 2/2013 |
| WO | WO 2014/066659 | 5/2014 |
| WO | WO 2014/124860 | 8/2014 |

OTHER PUBLICATIONS

Houslay et. al in Drug Discovery Today 10(22) 1503-1519 (2003) (Year: 2003).*
Holden et al. in Journal of Investigative Dermatology 87(3), 372-376 (1986) (Year: 1986).*
Holden, Colin A. et al., "Monocyte Localization of Elevated cAMP Phosphodiesterase Activity in Atopic Dermatitis," Journal of Investigative Dermatology, vol. 87, No. 3, pp. 372-376 (1986).
Houslay, Miles D. et al., "Phosphodiesterase-4 as a therapeutic agent," Drug Discovery Today, vol. 10, No. 22, pp. 1503-1519 (2005).
Smith, Victoria Boswell et al., "Selective phosphodiesterase 4 inhibitors in the treatment of allergy and inflammation." Curr. Opinion Investig. Drugs, vol. 6, No. 11, pp. 1136-1141 (2006).
Kroegel, Claus et al., "Phosphodiesterase-4 inhibitors as a novel approach for the treatment of respiratory disease: cilomilast," Exp. Opinion Investig. Drugs, vol. 16, No. 1, pp. 109-124 (2007)).
International Search Report for International Application No. PCT/EP2018/084974, dated Feb. 15, 2019. (4 pages).
Written Opinion of the International Search Authority for International Application No. PCT/EP2018/084974. (6 pages).

* cited by examiner

*Primary Examiner* — Dennis Heyer
(74) *Attorney, Agent, or Firm* — DLA Piper LLP (US)

(57) ABSTRACT

The present invention relates to novel substituted azetidine dihydrothienopyrimidines with phosphodiesterase inhibitory activity, and to their use in therapy, and to pharmaceutical compositions comprising the compounds and to methods of treating diseases with the compounds (I).

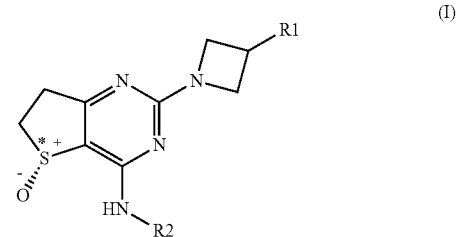

12 Claims, No Drawings

SUBSTITUTED AZETIDINE DIHYDROTHIENOPYRIMIDINES AND THEIR USE AS PHOSPHODIESTERASE INHIBITORS

This application is a national stage filing under 35 U.S.C. § 371 of International Application No. PCT/EP2018/084974, filed on Dec. 14, 2018, which claims priority to European Patent Application No. 17207659.8, filed on Dec. 15, 2017. The contents of these applications are each incorporated herein by reference.

FIELD OF THE INVENTION

The present invention relates to novel substituted azetidine dihydrothienopyrimidines with phosphodiesterase inhibitory activity, and to their use in therapy, and to pharmaceutical compositions comprising the compounds and to methods of treating diseases with the compounds.

BACKGROUND OF THE INVENTION

Phosphodiesterases are enzymes that catalyse the hydrolysis of cyclic AMP and/or cyclic GMP in cells to 5-AMP and 5-GMP, respectively, and as such they are critical to cellular regulation of cAMP or cGMP levels. Of the 11 phosphodiesterases identified so far, phosphodiesterase (PDE) 4, PDE7 and PDE8 are selective for cAMP. PDE4 is the most important modulator of cAMP expressed in immune and inflammatory cells such as neutrophils, macrophages and T-lymphocytes. As cAMP is a key second messenger in the modulation of inflammatory responses, PDE4 has been found to regulate inflammatory responses of inflammatory cells by modulating proinflammatory cytokines such as TNF-α, IL-2, IFN-γ, GM-CSF and LTB4. Inhibition of PDE4 has therefore become an attractive target for the therapy of inflammatory diseases such as asthma, chronic obstructive pulmonary disease (COPD), rheumatoid arthritis, atopic dermatitis, psoriasis, inflammatory bowel disease such as Crohn's disease etc. (M. D. Houslay et al., *Drug Discovery Today* 10 (22), 2005, pp. 1503-1519). As atopic dermatitis (AD) patients have increased PDE-activity, PDE4-inhibition would also appear to be a viable treatment of AD (Journal of Investigative Dermatology (1986), 87(3), 372-6).

The PDE4 gene family consists at least of four genes, A, B, C and D, which have a high degree of homology (V. Boswell Smith and D. Spina, *Curr. Opinion Investig. Drugs* 6(11), 2006, pp. 1136-1141). The four PDE4 isoforms are differentially expressed in different tissues and cell types. Thus, PDE4B is predominantly expressed in monocytes and neutrophils, but not in cortex and epithelial cells, while PDE4D is expressed in lung, cortex, cerebellum and T-cells (C. Kroegel and M. Foerster, *Exp. Opinion Investig. Drugs* 16(1), 2007, pp. 109-124).

Numerous PDE4 inhibitors have been studied for their therapeutic effect on inflammatory diseases, primarily asthma and COPD.

WO 2006/111549, US 20070259846, WO 2009/050236, WO 2009/050242, and WO 2009/053268, (all Boehringer Ingelheim International) each disclose dihydrothieno-pyrimidines which are substituted with piperazine for the treatment of respiratory or inflammatory diseases. The compounds are stated to inhibit the PDE4 enzyme.

WO 2007/118793, WO 2009/050248, and WO 2013/026797 (all Boehringer Ingelheim International) each disclose dihydrothieno-pyrimidines which are substituted with piperidine for the treatment of respiratory or inflammatory diseases. The compounds are stated to inhibit the PDE4 enzyme.

WO 2014/066659, Tetra Discovery Partners, discloses bicyclic heteroaryl compounds which are stated to be inhibitors of PDE4.

There is a continuous need for developing novel PDE4 inhibitors which have a more favourable therapeutic window, i.e. fewer adverse effects, while retaining their therapeutic effect.

SUMMARY OF THE INVENTION

It is an object of the present invention to provide novel azetidine dihydrothieno-pyrimidines. In one aspect the present invention relates to PDE4 inhibitors that could be useful as therapeutic agents for diseases mediated by PDE4, including dermal diseases or conditions, inflammatory allergic diseases, autoimmune diseases; acute or chronic cutaneous wound disorders, and the like.

The compounds of the present invention could have favourable oral bioavailability, solubility, absorption and metabolic stability. They could also have a favourable safety profile making them better tolerated than other PDE4 inhibitors.

The compounds of the present invention could have low clearance in human liver microsomes thus making them suitable for oral use.

The compounds of the present invention could have an improved window over nausea and emesis side effects, relative to other PDE4 inhibitors, thus allowing them to be dosed at higher multiples of their PDE4 potencies for greater therapeutic effect.

In one aspect the invention provides a compound of general formula (I)

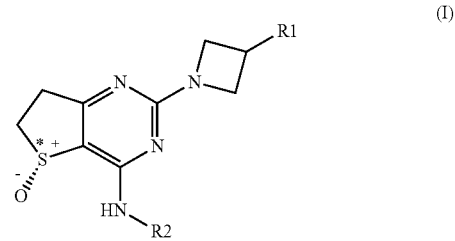

wherein $R^1$ is selected from the group consisting of phenyl, 6 membered heteroaryl, phenoxy and 6 membered heteroaryloxy; all of which are optionally substituted with one or more substituents independently selected from $R^3$; and $R^2$ is selected from the group consisting of $(C_3-C_7)$ cycloalkyl, bridged $(C_3-C_7)$cycloalkyl and (4-7 membered) heterocycloalkyl; all of which are optionally substituted with one or more substituents independently selected from $R^4$; and $R^3$ is selected from the group consisting of halogen, —CN, $(C_1-C_4)$alkyl, halo$(C_1-C_4)$alkyl, hydroxy$(C_1-C_4)$alkyl and $(C_3-C_6)$cycloalkyl; and $R^4$ is selected from the group consisting of fluoro, —CN, —OH, $(C_1-C_4)$alkyl, halo$(C_1-C_4)$alkyl, hydroxy$(C_1-C_4)$alkyl, —$OR^x$, —$S(O)_2R^x$, —$S(O)_2NR^aR^b$, —$C(O)R^x$, —$C(O)(OR^x)$, and —$C(O)NR^aR^b$; and $R^x$ is selected from the group consisting of $(C_1-C_4)$alkyl and $(C_3-C_6)$cycloalkyl; and $R^a$ and $R^b$ are independently selected from the group consisting of hydrogen, $(C_1-C_4)$alkyl and $(C_3-C_6)$cycloalkyl; and S* represents a chiral sulfur atom with (R) stereochemistry; and pharmaceutically acceptable salts, enantiomers, mixtures of enantiomers, diastereomers, mixtures of diastereomers, hydrates and solvates thereof.

In another aspect, the invention provides pharmaceutical compositions comprising a compound of the invention as defined above together with a pharmaceutically acceptable vehicle or excipient or pharmaceutically acceptable carrier(s), optionally together with one or more other therapeutically active compound(s).

In another aspect, the invention provides the use of a compound of the invention, for the manufacture of pharmaceutical compositions for the prophylaxis, treatment, prevention or amelioration of a disease, disorder or condition responsive to PDE4 inhibitory activity.

In yet another aspect the invention provides a method for treatment, prevention or alleviation of diseases, disorders or conditions responsive to PDE4 inhibitory activity, and which method comprises the step of administering to a living animal body a therapeutically effective amount of the compound of the invention.

Other objects of the invention will be apparent to the person skilled in the art from the following detailed description and examples.

DETAILED DESCRIPTION OF THE INVENTION

Definitions of the Invention

As used throughout the present specification and appended claims, the following terms have the indicated meaning:

The term "alkyl" is intended to indicate a radical obtained when one hydrogen atom is removed from a branched or linear hydrocarbon. Said alkyl comprises 1-6, such as 1-4, such as 1-3, such as 2-3 or such as 1-2 carbon atoms. The term includes the subclasses normal alkyl (n-alkyl), secondary and tertiary alkyl, such as methyl, ethyl, n-propyl, isopropyl, n-butyl, isobutyl, sec.-butyl, tert.-butyl, n-pentyl, isopentyl, neopentyl, n-hexyl and isohexyl.

The terms "alkyloxy" and "alkoxy" are intended to indicate a radical of the formula —OR', wherein R' is alkyl as indicated herein, wherein the alkyl group is appended to the parent molecular moiety through an oxygen atom, e.g. methoxy (—OCH$_3$), ethoxy (—OCH$_2$CH$_3$), n-propoxy, isopropoxy, butoxy, tert-butoxy, and the like.

The term "hydroxyalkyl" is intended to indicate an alkyl group as defined above substituted with one or more hydroxy, e.g. hydroxymethyl, hydroxyethyl, hydroxypropyl.

The term "halogen" is intended to indicate a substituent from the 7$^{th}$ main group of the periodic table, such as fluoro, chloro and bromo, preferably fluoro.

The term "haloalkyl" is intended to indicate an alkyl group as defined herein substituted with one or more halogen atoms as defined herein, e.g. fluoro or chloro, such as fluoromethyl, difluoromethyl or trifluoromethyl.

The terms "haloalkyloxy" and "haloalkoxy" are intended to indicate a haloalkyl group as defined herein which is appended to the parent molecular moiety through an oxygen atom, such as difluoromethoxy or trifluoromethoxy.

The term "cycloalkyl" is intended to indicate a saturated cycloalkane hydrocarbon radical, as described herein. Said cycloalkyl comprises 3-7 carbon atoms, such as 3-6 carbon atoms, such as 3-5 carbon atoms or such as 3-4 carbon atoms, e.g. cyclopropyl, cyclobutyl, cyclopentyl, cyclohexyl, or cycloheptyl.

The term "bridged cycloalkyl" is intended to indicate a saturated carbocyclic ring having the indicated number of carbon atoms and containing one or two carbon bridges. Representative examples include, but are not limited to, norbornyl, nortricyclyl, bicyclo[1.1.1]pentyl.

The term "heterocycloalkyl" is intended to indicate a cycloalkane radical as described herein, wherein one or more carbon atoms are replaced by heteroatoms, having a ring size of 4-7 atoms, comprising 1-6 carbon atoms, e.g. 2-5 or 2-4 carbon atoms, further comprising 1-3 heteroatoms, such as 1 heteroatom, such as 1-2 heteroatoms, such as 1-3 heteroatoms, such as 1-4 heteroatoms selected from O, N, or S, S(=O) or S(=O)$_2$. Representative examples of (4-7 membered) heterocycloalkyl groups include, but are not limited to azepanyl, azetidinyl, dioxolanyl, dioxolyl, dioxothietanyl, dioxothianyl, imidazolidinyl, morpholinyl, thiomorpholinyl, oxetanyl, piperazinyl, piperidinyl, pyrrolidinyl, tetrahydrofuranyl, tetrahydropyranyl, tetrahydrothiophenyl, tetrahydro-thiopyranyl.

The term "heteroaryl" is intended to indicate radicals of monocyclic heteroaromatic rings comprising 5- or 6-membered ring which contains from 1-5 carbon atoms and from 1-4 heteroatoms selected from O, N, or S. The heteroaryl radical may be connected to the parent molecular moiety through a carbon atom or a nitrogen atom contained anywhere within the heteroaryl group. Representative examples of (5-6) membered heteroaryl groups include, but are not limited to, furanyl, imidazolyl, isothiazolyl, isoxazolyl, oxadiazolyl, oxazolyl, pyrazinyl, pyrazolyl, pyridazinyl, pyridyl, pyrimidinyl, pyrrolyl, tetrazolyl, thiadiazolyl, thiazolyl, thienyl, triazolyl.

The term "6 membered heteroaryl" is intended to indicate radicals of monocyclic heteroaromatic rings, comprising a 6-membered ring, i.e. having a ring size of 6 atoms, which contain from 1-5 carbon atoms and from 1-5 heteroatoms, such as 1 heteroatom, such as 1-2 heteroatoms, such as 1-3 heteroatoms, such as 1-4 heteroatoms, where the heteroatom is N. Representative examples of 6 membered heteroaryl groups include, but are not limited to pyrazinyl, pyridazinyl, pyridyl, pyrimidinyl, and triazinyl.

The term "heteroaryloxy" as used herein refers to the radical heteroaryl-O—, where "heteroaryl" is as described above. Representative examples of 6 membered heteroaryloxy groups include, but are not limited to pyrazinyloxy, pyridazinyloxy, pyridyloxy, pyrimidinyloxy, triazinyloxy.

The term "hydrocarbon radical" is intended to indicate a radical containing only hydrogen and carbon atoms, it may contain one or more double and/or triple carbon-carbon bonds, and it may comprise cyclic moieties in combination with branched or linear moieties. Said hydrocarbon comprises 1-6 carbon atoms, and preferably comprises 1-5, e.g. 1-4, e.g. 1-3, e.g. 1-2 carbon atoms. The term includes alkyl, cycloalkyl and aryl, as indicated herein.

In some instances, the number of carbon atoms in a hydrocarbon radical (e.g. alkyl, cycloalkyl and aryl) is indicated by the prefix "$(C_a-C_b)$", wherein a is the minimum number and b is the maximum number of carbons in the hydrocarbon radical. Thus, for example $(C_1-C_4)$alkyl is intended to indicate an alkyl radical comprising from 1 to 4 carbon atoms, and $(C_3-C_6)$cycloalkyl is intended to indicate a cycloalkyl radical comprising from 3 to 6 carbon ring atoms.

The term "oxo" is intended to indicate an oxygen atom which is connected to the parent molecular moiety via a double bond (=O).

The group "CN" is intended to represent cyano.

The group "OH" is intended to represent hydroxy.

The group "C(O)" is intended to represent a carbonyl group (C=O).

The group "S(O)$_2$" is intended to represent a sulfonyl group (S(=O)$_2$).

If substituents are described as being independently selected from a group, each substituent is selected independent of the other. Each substituent may therefore be identical or different from the other substituent(s).

The term "optionally substituted" means "unsubstituted or substituted", and therefore the general formulas described herein encompasses compounds containing the specified optional substituent(s) as well as compounds that do not contain the optional substituent(s).

The term "pharmaceutically acceptable salt" is intended to indicate salts prepared by reacting a compound of formula I, which comprise a basic moiety, with a suitable inorganic or organic acid, such as hydrochloric, hydrobromic, hydroiodic, sulfuric, nitric, phosphoric, formic, acetic, 2,2-dichloroacetic, adipic, ascorbic, L-aspartic, L-glutamic, galactaric, lactic, maleic, L-malic, phthalic, citric, propionic, benzoic, glutaric, gluconic, D-glucuronic, methanesulfonic, salicylic, succinic, malonic, tartaric, benzenesulfonic, ethane-1,2-disulfonic, 2-hydroxy ethanesulfonic acid, toluenesulfonic, sulfamic, fumaric and ethylenediaminetetraacetic acid. Pharmaceutically acceptable salts of compounds of formula I comprising an acidic moiety may also be prepared by reaction with a suitable base such as sodium hydroxide, potassium hydroxide, magnesium hydroxide, calcium hydroxide, silver hydroxide, ammonia or the like, or suitable non-toxic amines, such as lower alkylamines, hydroxy-lower alkylamines, cycloalkylamines, or benzylamines, or L-arginine or L-lysine. Further examples of pharmaceutical acceptable salts are listed in Berge, S. M.; J. Pharm. Sci.; (1977), 66(1), 1-19, which is incorporated herein by reference.

The term "solvate" is intended to indicate a species formed by interaction between a compound, e.g. a compound of formula I, and a solvent, e.g. alcohol, glycerol or water, wherein said species are in a crystalline form. When water is the solvent, said species is referred to as a hydrate.

The term "protic solvent" is intended to indicate a solvent which has an acidic hydrogen, such as water, or such as alcohols, e.g. methanol, ethanol or isopropanol.

The term "aprotic solvent" is intended to indicate a solvent which does not have an acidic hydrogen, such as for example dichloromethane, acetonitrile, dimethyl-formamide, formamide, dimethyl sulfoxide or acetone.

The term "treatment" as used herein means the management and care of a patient for the purpose of combating a disease, disorder or condition. The term is intended to include the delaying of the progression of the disease, disorder or condition, the amelioration, alleviation or relief of symptoms and complications, and/or the cure or elimination of the disease, disorder or condition. The term may also include prevention of the condition, wherein prevention is to be understood as the management and care of a patient for the purpose of combating the disease, condition or disorder and includes the administration of the active compounds to prevent the onset of the symptoms or complications. Nonetheless, prophylactic (preventive) and therapeutic (curative) treatments are two separate aspects.

The terms "disease", "condition" and "disorder" as used herein are used interchangeably to specify a state of a patient which is not the normal physiological state of man.

The term "medicament" as used herein means a pharmaceutical composition suitable for administration of the pharmaceutically active compound to a patient.

The term "pharmaceutically acceptable" as used herein means suited for normal pharmaceutical applications, i.e. giving rise to no adverse events in patients etc.

EMBODIMENTS OF THE INVENTION

In one aspect the invention provides a compound of general formula (I)

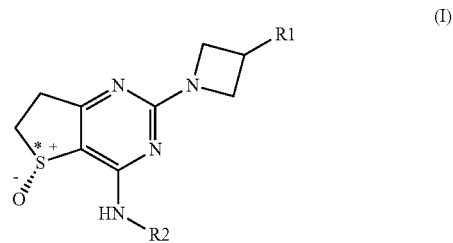

wherein $R^1$ is selected from the group consisting of phenyl, 6 membered heteroaryl, phenoxy and 6 membered heteroaryloxy; all of which are optionally substituted with one or more substituents independently selected from $R^3$; and $R^2$ is selected from the group consisting of $(C_3-C_7)$ cycloalkyl, bridged $(C_3-C_7)$cycloalkyl and (4-7 membered) heterocycloalkyl; all of which are optionally substituted with one or more substituents independently selected from $R^4$; and $R^3$ is selected from the group consisting of halogen, —CN, $(C_1-C_4)$alkyl, halo$(C_1-C_4)$alkyl, hydroxy$(C_1-C_4)$alkyl and $(C_3-C_6)$cycloalkyl; and $R^4$ is selected from the group consisting of fluoro, —CN, —OH, $(C_1-C_4)$alkyl, halo$(C_1-C_4)$alkyl, hydroxy$(C_1-C_4)$alkyl, —OR$^x$, —S(O)$_2$R$^x$, —S(O)$_2$NR$^a$R$^b$, —C(O)R$^x$, —C(O)(OR$^x$), and —C(O)NR$^a$R$^b$; and R$^x$ is selected from the group consisting of $(C_1-C_4)$alkyl and $(C_3-C_6)$cycloalkyl; and R$^a$ and R$^b$ are independently selected from the group consisting of hydrogen, $(C_1-C_4)$alkyl and $(C_3-C_6)$cycloalkyl; and S* represents a chiral sulfur atom with (R) stereochemistry; or pharmaceutically acceptable salts, enantiomers, mixtures of enantiomers, diastereomers, mixtures of diastereomers, hydrates and solvates thereof.

In another embodiment of the present invention, $R^1$ is selected from the group consisting of phenyl, pyridinyl, pyridyloxy and phenoxy; all of which are optionally substituted with one or more substituents independently selected from $R^3$.

In another embodiment of the present invention, $R^2$ is selected from the group consisting of tetrahydropyranyl, piperidinyl, pyrrolidinyl, dioxothietanyl, dioxothianyl, cyclobutyl and bicyclo[1.1.1]pentyl; all of which are optionally substituted with one or more substituents independently selected from $R^4$.

In another embodiment of the present invention, $R^3$ is fluoro or $(C_1-C_4)$alkyl.

In another embodiment of the present invention, $R^4$ is $(C_1-C_4)$alkyl or —C(O)(OR$^x$); and R$^x$ is $(C_1-C_4)$alkyl.

In another embodiment the invention provides a compound selected from the following:

(R)-2-(3-Phenylazetidin-1-yl)-4-((tetrahydro-2H-pyran-4-yl)amino)-6,7-dihydrothieno[3,2-d]pyrimidine 5-oxide,
(R)-2-(3-Phenoxyazetidin-1-yl)-4-((tetrahydro-2H-pyran-4-yl)amino)-6,7-dihydrothieno[3,2-d]pyrimidine 5-oxide,
(R)-2-(3-(4-Fluorophenoxy)azetidin-1-yl)-4-((tetrahydro-2H-pyran-4-yl)amino)-6,7-dihydrothieno[3,2-d]pyrimidine 5-oxide,
(R)-3-((5-Oxido-2-(3-phenylazetidin-1-yl)-6,7-dihydrothieno[3,2-d]pyrimidin-4-yl)amino)thietane 1,1-dioxide,
Methyl (3S)-3-(((5R)-5-oxido-2-(3-phenylazetidin-1-yl)-6,7-dihydrothieno[3,2-d]pyrimidin-4-yl)amino)pyrrolidine-1-carboxylate,
Methyl (3R)-3-(((5R)-5-Oxido-2-(3-phenylazetidin-1-yl)-6,7-dihydrothieno[3,2-d]pyrimidin-4-yl)amino)pyrrolidine-1-carboxylate,
Methyl (3R)-3-(((5R)-2-(3-(4-Fluorophenoxy)azetidin-1-yl)-5-oxido-6,7-dihydrothieno[3,2-d]pyrimidin-4-yl)amino)piperidine-1-carboxylate,
Methyl (3S)-3-(((5R)-2-(3-(4-Fluorophenoxy)azetidin-1-yl)-5-oxido-6,7-dihydrothieno[3,2-d]pyrimidin-4-yl)amino)piperidine-1-carboxylate,
(R)-4-(Bicyclo[1.1.1]pentan-1-ylamino)-2-(3-(4-fluorophenyl)azetidin-1-yl)-6,7-dihydrothieno[3,2-d]pyrimidine 5-oxide,
(R)-4-(Bicyclo[1.1.1]pentan-1-ylamino)-2-(3-(4-fluorophenoxy)azetidin-1-yl)-6,7-dihydrothieno[3,2-d]pyrimidine 5-oxide,
(R)-4-(Bicyclo[1.1.1]pentan-1-ylamino)-2-(3-phenylazetidin-1-yl)-6,7-dihydrothieno[3,2-d]pyrimidine 5-oxide,
(R)-4-(Bicyclo[1.1.1]pentan-1-ylamino)-2-(3-(pyridin-2-yl)azetidin-1-yl)-6,7-dihydrothieno[3,2-d]pyrimidine 5-oxide,
(R)-4-(Bicyclo[1.1.1]pentan-1-ylamino)-2-(3-(3-fluorophenyl)azetidin-1-yl)-6,7-dihydrothieno[3,2-d]pyrimidine 5-oxide,
(R)-4-(Bicyclo[1.1.1]pentan-1-ylamino)-2-(3-(pyridin-3-yloxy)azetidin-1-yl)-6,7-dihydrothieno[3,2-d]pyrimidine 5-oxide,
(R)-4-((1-Methylcyclobutyl)amino)-2-(3-(pyridin-2-yl)azetidin-1-yl)-6,7-dihydrothieno[3,2-d]pyrimidine 5-oxide,
(R)-4-((1-Methylcyclobutyl)amino)-2-(3-(pyridin-3-yl)azetidin-1-yl)-6,7-dihydrothieno[3,2-d]pyrimidine 5-oxide,
(5R)—N-(1,1-Dioxothian-4-yl)-5-oxido-2-(3-phenylazetidin-1-yl)-6,7-dihydrothieno[3,2-d]pyrimidin-4-yl-amine,
or a pharmaceutically acceptable salt, enantiomer, mixture of enantiomers, diastereomer, mixture of diastereomers, hydrate and solvate thereof.

The compounds of the invention may be obtained in crystalline form either directly by concentration from an organic solvent or by crystallisation or re-crystallisation from an organic solvent or mixture of said solvent and a co-solvent that may be organic or inorganic, such as water. The crystals may be isolated in essentially solvent-free form or as a solvate, such as a hydrate. The invention covers all crystalline forms, such as polymorphs and pseudopolymorphs, and also mixtures thereof.

The compounds of the invention may or may not comprise asymmetrically substituted (chiral) carbon atoms which give rise to the existence of isomeric forms, e.g. enantiomers and possibly diastereomers. The present invention relates to all such isomers, either in optically pure form or as mixtures thereof (e.g. racemic mixtures or partially purified optical mixtures). Pure stereoisomeric forms of the compounds and the intermediates of this invention may be obtained by the application of procedures known in the art. The various isomeric forms may be separated by physical separation methods such as selective crystallization and chromatographic techniques, e.g. high pressure liquid chromatography using chiral stationary phases. Enantiomers may be separated from each other by selective crystallization of their diastereomeric salts which may be formed with optically active amines or with optically active acids. Optically purified compounds may subsequently be liberated from said purified diastereomeric salts. Enantiomers may also be resolved by the formation of diastereomeric derivatives. Alternatively, enantiomers may be separated by chromatographic techniques using chiral stationary phases. Pure stereoisomeric forms may also be derived from the corresponding pure stereoisomeric forms of the appropriate starting materials, provided that the reaction occur stereoselectively or stereospecifically. If a specific stereoisomer is desired, said compound will be synthesized by stereoselective or stereospecific methods of preparation. These methods will advantageously employ chiral pure starting materials. Furthermore, when a double bond or a fully or partially saturated ring system is present in the molecule geometric isomers may be formed. It is intended that any geometric isomer, as separated, pure or partially purified geometric isomers or mixtures thereof are included within the scope of the invention.

The present invention is intended to include all isotopes of atoms occurring in the present compounds. Isotopes include those atoms having the same atomic number but different mass numbers. By way of general example and without limitation, isotopes of hydrogen include deuterium and tritium. Isotopes of carbon include $^{13}C$ and $^{14}C$. Isotopically-labelled compounds of the invention can generally be prepared by conventional techniques known to those skilled in the art or by processes analogous to those described herein, using an appropriate isotopically-labelled reagent in place of the non-labelled reagent otherwise employed.

Medical Use

As the Compounds of the invention could exhibit PDE4 inhibitory activity, the Compounds could be useful as therapeutic agents for inflammatory allergic diseases such as bronchial asthma, COPD, allergic rhinitis, and nephritis; autoimmune diseases such as rheumatoid arthritis, multiple sclerosis, Crohn's disease ulcerative colitis, virtiligo, lupus, systemic lupus erythematosus, and discoid lupus erythematosus; acute or chronic cutaneous wound disorders; diseases of the central nervous system such as depression, amnesia, and dementia; organopathy associated with ischemic reflux caused by cardiac failure, shock, and cerebrovascular diseases, and the like; insulin-resistant diabetes; wounds, and the like.

In one embodiment, the Compounds of the present invention are considered useful for the treatment, prevention or alleviation of dermal diseases or conditions.

In another embodiment, the Compounds of the present invention are considered useful for the treatment, prevention or alleviation of dermal diseases or conditions selected from the group consisting of proliferative and inflammatory skin disorders, dermatitis, atopic dermatitis, seborrheic dermatitis, contact dermatitis, including irritative contact dermatitis and allergic contact dermatitis, hand dermatitis, psoriasis, psoriasis vulgaris, inverse psoriasis, psoriatic arthritis, spondyloarthritis, epidermal inflammation, alopecia, alopecia areata, rosacea, skin atrophy, steroid induced skin atrophy, photo skin ageing, SAPHO syndrome, (synovitis, acne, pustulosis, hyperostosis and osteitis), acne vulgaris, hidradenitis suppurativa, urticaria, pruritis, and eczema.

In another embodiment, the Compounds of the present invention are considered useful for the treatment or alleviation of atopic dermatitis.

In another embodiment, the Compounds of the present invention are considered useful for the treatment or alleviation of psoriasis, psoriasis vulgaris, inverse psoriasis or psoriatic arthritis.

In another embodiment, the Compounds of the present invention are considered useful for the treatment or alleviation of psoriasis.

In another embodiment, the Compounds of the present invention are considered useful for the treatment or alleviation of alopecia areata.

In another embodiment, the Compounds of the present invention are considered useful for the treatment or alleviation of acne.

In another embodiment, the Compounds of the present invention are considered useful for the treatment or alleviation of pruritis.

In another embodiment, the Compounds of the present invention are considered useful for the treatment or alleviation of eczema.

Compounds of the invention, optionally in combination with other active compounds, could be useful for the treatment of dermal diseases or conditions, in particular for the treatment of proliferative and inflammatory skin disorders, dermatitis, atopic dermatitis, seborrheic dermatitis, contact dermatitis, including irritative contact dermatitis and allergic contact dermatitis, hand dermatitis, psoriasis, psoriasis vulgaris, inverse psoriasis, psoriatic arthritis, spondyloarthritis, epidermal inflammation, alopecia, alopecia areata, rosacea, skin atrophy, steroid induced skin atrophy, photo skin ageing, SAPHO syndrome, (synovitis, acne, pustulosis, hyperostosis and osteitis), acne vulgaris, hidradenitis suppurativa, urticaria, pruritis, and eczema.

Besides being useful for human treatment, the compounds of the present invention could also be useful for veterinary treatment of animals including mammals such as horses, cattle, sheep, pigs, dogs, and cats.

Pharmaceutical Compositions of the Invention

For use in therapy, compounds of the present invention are typically in the form of a pharmaceutical composition. The invention therefore relates to a pharmaceutical composition comprising a compound of formula (I), optionally together with one or more other therapeutically active compound(s), together with a pharmaceutically acceptable excipient or vehicle. The excipient must be "acceptable" in the sense of being compatible with the other ingredients of the composition and not deleterious to the recipient thereof.

Conveniently, the active ingredient comprises from 0.0001-50% by weight of the formulation.

In the form of a dosage unit, the compound could be administered one or more times a day at appropriate intervals, always depending, however, on the condition of the patient, and in accordance with the prescription made by the medical practitioner. Conveniently, a dosage unit of a formulation contain between 0.001 mg and 1000 mg, preferably between 0.01 mg and 250 mg, such as 0.1-100 mg of a compound of formula (I).

A suitable dosage of the compound of the invention will depend, inter alia, on the age and condition of the patient, the severity of the disease to be treated and other factors well known to the practising physician. The compound could be administered either orally, parenterally or topically according to different dosing schedules, e.g. daily or with weekly intervals. In general a single dose will be in the range from 0.001 to 10 mg/kg body weight, e.g. in the range from 0.01 to 5 mg/kg body weight. The compound could be administered as a bolus (i.e. the entire daily dose is administered at once) or in divided doses two or more times a day.

In the context of topical treatment it could be more appropriate to refer to a "usage unit", which denotes unitary, i.e. a single dose which is capable of being administered to a patient, and which could be readily handled and packed, remaining as a physically and chemically stable unit dose comprising either the active material as such or a mixture of it with solid or liquid pharmaceutical diluents or carriers. A "usage unit" is capable of being administered topically to a patient in an application per square centimetre of the skin of from 0.1 mg to 50 mg and preferably from 0.2 mg to 5 mg of the final formulation in question It is also envisaged that in certain treatment regimes, administration with longer intervals, e.g. every other day, every week, or even with longer intervals could be beneficial.

If the treatment involves administration of another therapeutically active compound it is recommended to consult *Goodman & Gilman's The Pharmacological Basis of Therapeutics*, 9$^{th}$ Ed., J. G. Hardman and L. E. Limbird (Eds.), McGraw-Hill 1995, for useful dosages of said compounds.

The administration of a compound of the present invention with one or more other active compounds could be either concomitantly or sequentially.

The formulations include e.g. those in a form suitable for oral (including sustained or timed release), rectal, parenteral (including subcutaneous, intraperitoneal, intramuscular, intraarticular and intravenous), transdermal, ophthalmic, topical, dermal, nasal or buccal administration.

The formulations may conveniently be presented in dosage unit form and may be prepared by but not restricted to any of the methods well known in the art of pharmacy, e.g. as disclosed in Remington, *The Science and Practice of Pharmacy,* 21ed ed., 2005. All methods include the step of bringing the active ingredient into association with the carrier, which constitutes one or more accessory ingredients. In general, the formulations are prepared by uniformly and intimately bringing the active ingredient into association with a liquid carrier, semisolid carrier or a finely divided solid carrier or combinations of these, and then, if necessary, shaping the product into the desired formulation.

For oral administration, including sustained or timed release, the compound of formula (I) could typically be present in an amount of from 0.001 to 20% by weight of the composition, such as 0.01% to about 10%.

Formulations of the present invention suitable for oral and buccal administration could be in the form of discrete units as capsules, sachets, tablets, chewing gum or lozenges, each containing a predetermined amount of the active ingredient; in the form of a powder, granules or pellets; in the form of a solution or a suspension in an aqueous liquid or non-aqueous liquid, such as ethanol or glycerol; or in the form of a gel, a nano- or microemulsion, an oil-in-water emulsion, a water-in-oil emulsion or other dispensing systems. The oils may be edible oils, such as but not restricted to e.g. cottonseed oil, sesame oil, coconut oil or peanut oil. Suitable dispersing or suspending agents for aqueous suspensions include synthetic or natural surfactants and viscosifying agents such as but not restricted to tragacanth, alginate, acacia, dextran, sodium carboxymethylcellulose, gelatin, methylcellulose, hydroxypropyl-methylcellulose, hydroxypropylcellulose, carbomers, polyvinylpyrrolidone, polysorbates, sorbitan fatty acid esters. The active ingredients could also be administered in the form of a bolus, electuary or paste.

A tablet may be made by compressing, moulding or freeze drying the active ingredient optionally with one or more accessory ingredients. Compressed tablets may be prepared by compressing, in a suitable machine, the active ingredient(s) in a free-flowing form such as a powder or granules, optionally mixed by a binder and/or filler, such as e.g. lactose, glucose, mannitol starch, gelatine, acacia gum, tragacanth gum, sodium alginate, calcium phosphates, microcrystalline cellulose, carboxymethylcellulose, methylcellulose, hydroxypropylcellulose, hydroxypropylmethylcellulose, ethylcellulose, hydroxyethylcellulose, polyethylene glycol, waxes or the like; a lubricant such as e.g. sodium oleate, sodium stearate, magnesium stearate, sodium benzoate, sodium acetate, sodium chloride or the like; a disintegrating agent such as e.g. starch, methylcellulose, agar, bentonite, croscarmellose sodium, sodium starch glycollate, crospovidone or the like or a dispersing agent, such as polysorbate 80. Moulded tablets may be made by moulding, in a suitable machine, a mixture of the powdered active ingredient and suitable carrier moistened with an inert liquid diluent. Freeze dried tablets may be formed in a freeze-dryer from a solution of the drug substance. A suitable filler can be included.

Formulations for rectal administration may be in the form of suppositories in which the compound of the present invention is admixed with low melting point, water soluble or insoluble solids such as cocoa butter, hydrogenated vegetable oils, polyethylene glycol or fatty acids esters of polyethylene glycols, while elixirs may be prepared using myristyl palmitate.

Formulations suitable for parenteral administration conveniently comprise a sterile oily or aqueous preparation of the active ingredients, which is preferably isotonic with the blood of the recipient, e.g. isotonic saline, isotonic glucose solution or buffer solution. Furthermore, the formulation may contain cosolvent, solubilising agent and/or complexation agents. The formulation may be conveniently sterilised by for instance filtration through a bacteria retaining filter, addition of sterilising agent to the formulation, irradiation of the formulation or heating of the formulation. Liposomal formulations as disclosed in e.g. Encyclopedia of Pharmaceutical Technology, vol. 9, 1994, are also suitable for parenteral administration.

Alternatively, the compounds of formula (I) could be presented as a sterile, solid preparation, e.g. a freeze-dried powder, which is readily dissolved in a sterile solvent immediately prior to use.

Transdermal formulations may be in the form of a plaster, patch, microneedles, liposomal or nanoparticulate delivery systems or other cutaneous formulations applied to the skin.

Formulations suitable for ophthalmic administration may be in the form of a sterile aqueous preparation of the active ingredients, which may be in micro-crystalline form, for example, in the form of an aqueous microcrystalline suspension. Liposomal formulations or biodegradable polymer systems e.g. as disclosed in Encyclopedia of Pharmaceutical Technology, vol. 2, 1989, may also be used to present the active ingredient for ophthalmic administration.

Formulations suitable for topical, such as dermal, intradermal or ophthalmic administration include liquid or semi-solid preparations such as liniments, lotions, gels, applicants, sprays, foams, film forming systems, microneedles, micro- or nano-emulsions, oil-in-water or water-in-oil emulsions such as creams, ointments or pastes; or solutions or suspensions such as drops. Compositions for ophthalmic treatment may additionally contain cyclodextrin.

For topical administration, the compound of formula (I) could typically be present in an amount of from 0.001 to 20% by weight of the composition, such as 0.01% to about 10%, but could also be present in an amount of up to about 100% of the composition.

Formulations suitable for nasal or buccal administration include powder, self-propelling and spray formulations, such as aerosols and atomisers. Such formulations are disclosed in greater detail in e.g. Modern Pharmaceutics, $2^{nd}$ ed., G. S. Banker and C. T. Rhodes (Eds.), page 427-432, Marcel Dekker, New York; Modern Pharmaceutics, $3^{th}$ ed., G. S. Banker and C. T. Rhodes (Eds.), page 618-619 and 718-721, Marcel Dekker, New York and Encyclopedia of Pharmaceutical Technology, vol. 10, J. Swarbrick and J. C. Boylan (Eds), page 191-221, Marcel Dekker, N.Y.

In addition to the aforementioned ingredients, the formulations of a compound of formula (I) may include one or more additional ingredients such as diluents, buffers, flavouring agents, colourant, surface active agents, thickeners, penetration enhancing agents, solubility enhancing agents preservatives, e.g. methyl hydroxybenzoate (including antioxidants), emulsifying agents and the like.

When the active ingredient is administered in the form of salts with pharmaceutically acceptable non-toxic acids or bases, preferred salts are for instance easily water-soluble or slightly soluble in water, in order to obtain a particular and appropriate rate of absorption.

The pharmaceutical composition may additionally comprise one or more other active components conventionally used in the treatment of dermal disease or conditions, e.g. selected from the group consisting of glucocorticoids, vitamin D and vitamin D analogues, antihistamines, platelet activating factor (PAF) antagonists, anticholinergic agents, methylxanthines, β-adrenergic agents, COX-2 inhibitors, JAK inhibitors, other PDE inhibitors, salicylates, indomethacin, flufenamate, naproxen, timegadine, gold salts, penicillamine, serum cholesterol lowering agents, retinoids, zinc salts, salicylazosulfapyridine and calcineurin inhibitors.

Methods of Preparation

The compounds of the present invention can be prepared in a number of ways well known to those skilled in the art of synthesis. The compounds of the invention could for example be prepared using the reactions and techniques outlined below together with methods known in the art of synthetic organic chemistry, or variations thereof as appreciated by those skilled in the art. Preferred methods include, but are not limited to, those described below. The reactions are carried out in solvents appropriate to the reagents and materials employed and suitable for the transformations being effected. Also, in the synthetic methods described below, it is to be understood that all proposed reaction conditions, including choice of solvent, reaction atmosphere, reaction temperature, duration of experiment and work-up procedures, are chosen to be conditions of standard for that reaction, which should be readily recognized by one skilled in the art. Not all compounds falling into a given class may be compatible with some of the reaction conditions required in some of the methods described. Such restrictions to the substituents which are compatible with the reaction conditions will be readily apparent to one skilled in the art and alternative methods can be used.

The compounds of the present invention or any intermediate could be purified, if required, using standard methods well known to a synthetic organist chemist, e.g. methods described in "Purification of Laboratory Chemicals", $6^{th}$ ed. 2009, W. Amarego and C. Chai, Butterworth-Heinemann.

Starting materials are either known or commercially available compounds, or may be prepared by routine synthetic methods well known to a person skilled in the art. Unless otherwise noted, reagents and solvents were used as received from commercial suppliers. Proton nuclear magnetic resonance spectra were obtained on a Bruker AVANCE 400 spectrometer at 400 MHz, and Bruker AVANCE 500 spectrometer at 500 MHz. Tetramethylsilane was used as an internal standard for proton spectra. The value of a multiplet, either defined doublet (d), triplet (t), quartet (q) or (m) at the approximate midpoint is given unless a range is quoted. (br) indicates a broad peak, whilst (s) indicates a singlet. Thin layer chromatography was performed using Merck 60F254 silica-gel TLC plates. Visualisation of TLC plates was performed using UV light (254 nm). Mass spectra were obtained on a Shimadzu LCMS-2010EV spectrometer using electrospray ionization (ESI) and/or atmospheric-pressure chemical ionization (APCI).

The following abbreviations have been used throughout:
ABPR automated back pressure regulator
DEA diethylamine
DCM dichloromethane
DIPEA diisopropylethylamine
DMF N,N-dimethylformamide
DMSO dimethylsulfoxide
EtOAc ethyl acetate
EtOH ethanol
HPLC high-performance liquid chromatograph
LCMS liquid chromatography-mass spectrometry
Me methyl
MeCN acetontitrile
MeOH methanol
MHz megahertz
NMP N-methyl-2-pyrrolidinone
NMR nuclear magnetic resonance
ppm parts per million
SFC supercritical fluid chromatography
TLC thin layer chromatography General Methods Compounds of the invention may be prepared according to the following non-limiting general methods and examples:

Scheme 1

Synthesis of a compound of general formula (I), wherein $R^1$ and $R^2$ are as previously defined:

Compounds of general formula (Int1) can be prepared, as shown in Scheme 1, by reaction of commercially available 2,4-dichloro-6,7-dihydrothieno[3,2-d]pyrimidine with an amine of formula $R^1NH_2$. Typical reaction conditions involve heating a solution of 2,4-dichloro-6,7-dihydrothieno[3,2-d]pyrimidine and the appropriate amine in a suitable protic, or polar aprotic, solvent at a temperature between room temperature and the boiling point of the solvent, in the presence of an added organic or inorganic base. The amines $R^1NH_2$ are commercially available or can readily be synthesised by methods known to those skilled in the art.

Typical conditions comprise reacting 2,4-dichloro-6,7-dihydrothieno[3,2-d]pyrimidine with an amine of formula $R^1NH_2$ in DMF in the presence of DIPEA at 120° C. as exemplified in Preparation 1.

Alternatively, compounds of general formula (Int1) can be prepared from 2,4-dichloro-6,7-dihydrothieno[3,2-d]pyrimidine by reaction with an amine of formula $R^1NH_2$ in a suitable solvent, or solvent mixture, such as 1,4-dioxane, in the presence of a palladium catalyst and a suitable inorganic or organic base, such as potassium $^t$butoxide, potassium carbonate or caesium carbonate.

Sulfoxides of general formula (Int2) can be prepared, as shown in Scheme 1, by reaction of compounds of general formula (Int1) with a suitable oxidising agent in an appropriate solvent, optionally in the presence of a chiral catalyst. For example, a solution of compounds of general formula (Int1) in DCM/water can be oxidised by treatment with $^t$BuOOH, at a temperature between 0° C. and room temperature, in the presence of Ti($^i$OPr)$_4$ and (S)(−)-1,1'-bi(2-naphthol), as outlined in Preparation 9. Sulfoxides of general formula (Int2) can be prepared as single enantiomers or, alternatively, as mixtures of enantiomers which are then separated by methods know to those skilled in the art. Alternatively it may be preferable to take compounds forward as mixtures of enantiomers and separate the enantiomers at a later stage, as described in Example 9.

Compounds of general formula (I) can be prepared, as shown in Scheme 1, by reaction of compounds of general formula (Int2) with amines of general formula (Int3), which are either commercially available or can readily be synthesised by methods known to those skilled in the art.

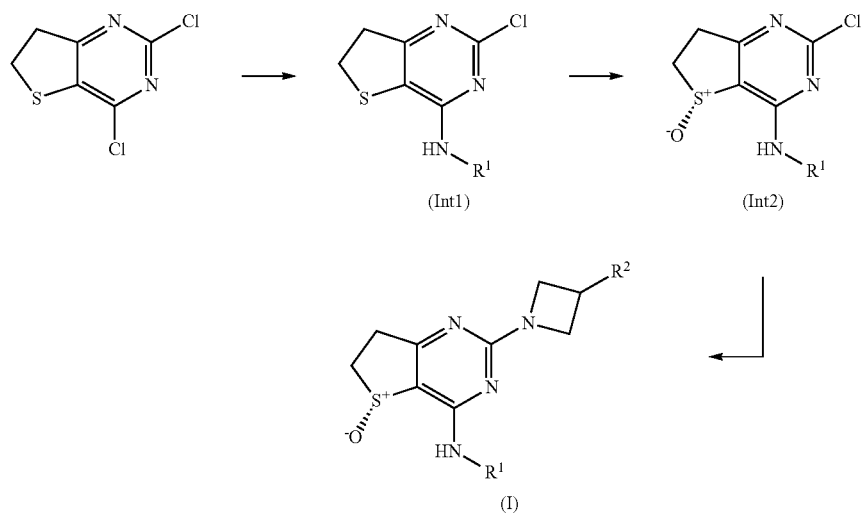

(Int3)

Typical reaction conditions involve reacting compounds of formula (Int2) and the appropriate amine of formula (Int3) in a suitable protic, or polar aprotic, solvent at a temperature between room temperature and the boiling point of the solvent, in the presence of an added organic or inorganic base. For example, a solution of a compound of formula (Int2) in NMP can be reacted with an amine of formula (Int3) at 100° C. in the presence of DIPEA, as outlined in Example 1.

Alternatively, compounds of general formula (I) can be prepared from compounds of formula (Int2) by reaction with an amine of formula (Int3) in a suitable solvent, or solvent mixture, such as 1,4-dioxane, in the presence of a palladium catalyst and a suitable inorganic or organic base, such as potassium ᵗbutoxide, potassium carbonate or caesium carbonate.

PREPARATIONS AND EXAMPLES

Preparation 1

2-Chloro-N-(tetrahydro-2H-pyran-4-yl)-6,7-dihydrothieno[3,2-d]pyrimidin-4-amine

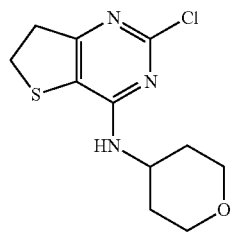 [SMILES: Clc1nc2c(c(NC3CCOCC3)n1)SCC2]

DIPEA (62.31 g, 483 mmol) was added at room temperature to a stirred solution of 2,4-dichloro-6,7-dihydrothieno[3,2-d]pyrimidine (50.0 g, 242 mmol) and tetrahydropyran-4-amine (29.3 g, 290 mmol) in DMF (150 mL). The mixture was then heated for 2 hours under a $N_2$ atmosphere in a sealed tube at 120° C. The reaction mass allowed to cool to room temperature and poured into ice cold water. The resulting solid was filtered off and washed with water, diethyl ether and a toluene/DCM mixture (2:1 ratio). The solid was dried under reduced pressure to afford the pure title compound as a solid. $^1$H NMR (DMSO-d6, 400 MHz): δ (ppm) 7.20-7.13 (m, 1H), 4.16-3.95 (m, 1H), 3.90-3.84 (m, 2H), 3.42-3.32 (m, 4H), 3.20-3.07 (m, 2H), 1.81-1.68 (m, 2H), 1.62-1.56 (m, 2H); LCMS (ESI): m/z 272 [M+H]⁺; 97.6%; RT=1.8 min; (AQUITY UPLC BEH C18 column, 0.1% FORMIC ACID in water with MeCN).

Preparation 2

3-((2-Chloro-6,7-dihydrothieno[3,2-d]pyrimidin-4-yl)amino)thietane-1,1-dioxide

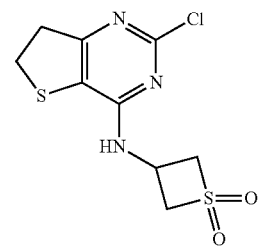 [SMILES: O=S1(=O)CC(Nc2nc(Cl)nc3c2SCC3)C1]

The title compound was prepared in the same manner as the compound of Preparation 1 from 2,4-dichloro-6,7-dihydrothieno[3,2-d]pyrimidine and 1,1-dioxothietan-3-amine, and was obtained as a solid. $^1$H NMR (DMSO-d6, 300 MHz): δ (ppm) 7.97 (s, 1H), 4.63-4.46 (m, 3H), 4.32-4.20 (m, 2H), 3.45-3.36 (m, 2H), 3.21-3.08 (m, 1H); LCMS (ESI): m/z 292 [M+H]⁺; 99%; RT=1.98 min; (AQUITY UPLC BEH C18 column, 0.1% FORMIC ACID in water with MeCN).

Preparation 3

Methyl (S)-3-((2-chloro-6,7-dihydrothieno[3,2-d]pyrimidin-4-yl)amino)pyrrolidine-1-carboxylate

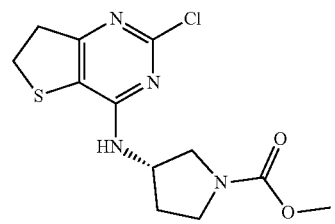 [SMILES: COC(=O)N1CC[C@H](Nc2nc(Cl)nc3c2SCC3)C1]

The title compound was prepared in the same manner as the compound of Preparation 1 from 2,4-dichloro-6,7-dihydrothieno[3,2-d]pyrimidine and methyl (3S)-3-aminopyrrolidine-1-carboxylate, and was obtained as a solid.

Preparation 4

Methyl (R)-3-((2-chloro-6,7-dihydrothieno[3,2-d]pyrimidin-4-yl)amino)pyrrolidine-1-carboxylate

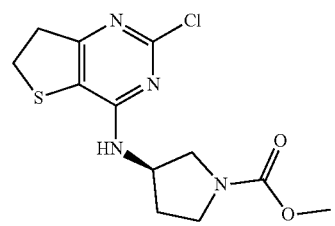 [SMILES: COC(=O)N1CC[C@@H](Nc2nc(Cl)nc3c2SCC3)C1]

The title compound was prepared in the same manner as the compound of Preparation 1 from 2,4-dichloro-6,7-dihydrothieno[3,2-d]pyrimidine and methyl (3R)-3-amino-pyrrolidine-1-carboxylate, and was obtained as a solid. ¹H NMR (DMSO-d6, 500 MHz): δ (ppm) 7.52-7.45 (m, 1H), 4.55-4.44 (m, 1H), 3.62-3.56 (m, 4H), 3.48-3.40 (m, 1H), 3.38-3.33 (m, 3H), 3.26-3.21 (m, 1H), 3.18-3.13 (m, 2H), 2.16-2.07 (m, 1H), 1.98-1.91 (m, 1H); LCMS (ESI): m/z 315 [M+H]$^+$; 99%; RT=1.90 min; (AQUITY UPLC BEH C18 column, 0.1% FORMIC ACID in water with MeCN).

Preparation 5

Methyl (R)-3-((2-chloro-6,7-dihydrothieno[3,2-d]pyrimidin-4-yl)amino)piperidine-1-carboxylate

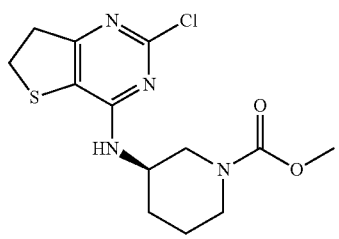 [SMILES: COC(=O)N1CCC[C@@H](Nc2nc(Cl)nc3c2SCC3)C1]

The title compound was prepared in the same manner as the compound of Preparation 1 from 2,4-dichloro-6,7-dihydrothieno[3,2-d]pyrimidine and methyl (3R)-3-aminopiperidine-1-carboxylate, and was obtained as a solid. ¹H NMR (400 MHz, DMSO-d6) δ=7.17-7.12 (m, 1H), 4.04-3.80 (m, 3H), 3.59 (s, 3H), 3.40-3.34 (m, 2H), 3.18-3.12 (m, 2H), 2.79-2.69 (m, 2H), 1.89-1.83 (m, 1H), 1.74-1.67 (m, 1H), 1.59-1.40 (m, 2H).

Preparation 6

Methyl (S)-3-((2-chloro-6,7-dihydrothieno[3,2-d]pyrimidin-4-yl)amino)piperidine-1-carboxylate

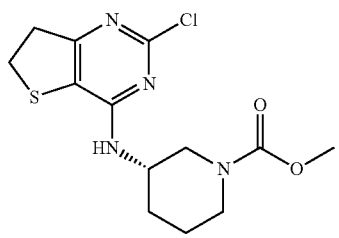 [SMILES: COC(=O)N1CCC[C@H](Nc2nc(Cl)nc3c2SCC3)C1]

The title compound was prepared in the same manner as the compound of Preparation 1 from 2,4-dichloro-6,7-dihydrothieno[3,2-d]pyrimidine and methyl (3S)-3-aminopiperidine-1-carboxylate, and was obtained as a solid. ¹H NMR (400 MHz, DMSO-d6) δ=7.20-7.12 (m, 1H), 4.09-3.78 (m, 3H), 3.59 (s, 3H), 3.41-3.35 (m, 2H), 3.19-3.10 (m, 2H), 2.80-2.72 (m, 2H), 1.92-1.84 (m, 2H), 1.75-1.69 (m, 2H) LCMS (ESI): m/z 329 [M+H]$^+$; 98%; RT=1.70 min; (AQUITY UPLC BEH C18 column, 0.1% FORMIC ACID in water with MeCN).

Preparation 7

N-(Bicyclo[1.1.1]pentan-1-yl)-2-chloro-6,7-dihydrothieno[3,2-d]pyrimidin-4-amine

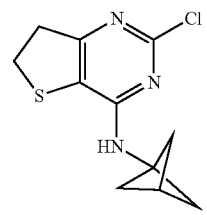

The title compound was prepared in the same manner as the compound of Preparation 1 from 2,4-dichloro-6,7-dihydrothieno[3,2-d]pyrimidine and bicyclo[1.1.1]pentan-3-amine, and was obtained as a solid. ¹H NMR (CDCl₃, 300 MHz): δ (ppm) 4.82-4.76 (m, 1H), 3.48-3.34 (m, 2H), 3.29-3.18 (m, 2H), 2.52 (s, 1H), 2.20 (s, 6H), 1.58-1.51 (m, 1H), 1.45 (d, J=6.6 Hz, 1H).

Preparation 8

2-Chloro-N-(1-methylcyclobutyl)-6,7-dihydrothieno[3,2-d]pyrimidin-4-amine

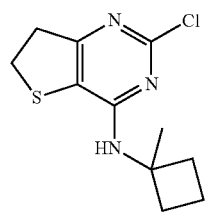

The title compound was prepared in the same manner as the compound of Preparation 1 from 2,4-dichloro-6,7-dihydrothieno[3,2-d]pyrimidine and 1-methylcyclobutan-amine, and was obtained as a solid. ¹H NMR (DMSO-d6, 400 MHz): δ (ppm) 7.28 (s, 1H), 3.38-3.32 (m, 2H), 3.17-3.07 (m, 2H), 2.33-2.18 (m, 2H), 2.06-1.96 (m, 2H), 1.84-1.72 (m, 2H), 1.47 (s, 3H); LCMS (ESI): m/z 256 [M+H]$^+$; 95.7%; RT=2.1 min; (AQUITY UPLC BEH C18 column, 0.1% FORMIC ACID in water with MeCN).

Preparation 9

(R)-2-Chloro-4-((tetrahydro-2H-pyran-4-yl)amino)-6,7-dihydrothieno[3,2-d]pyrimidine-5-oxide

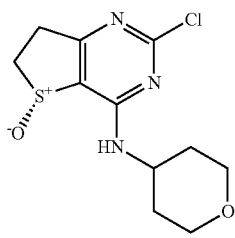

Ti($^i$OPr)$_4$ (0.25 g, 0.90 mmol) was added to a stirred solution of the compound of Preparation 1 (5.0 g, 18.1 mmol) and (S)(−)-1,1'-bi(2-naphthol) (0.51 g, 1.81 mmol) in water/DCM (6.5 mL, 5:1 ratio) at room temperature under N$_2$ and the reaction was stirred for 1 hour. The reaction was then cooled to 0° C. and $^t$BuOOH (5.0 mL, 19.9 mmol) was added slowly. After completion of the reaction (monitored by TLC) the DCM was completely distilled out and 250 mL of hot MeOH (50° C.) was added. The precipitated solid was filtered off through a celite pad and the filtrate was concentrated under reduced pressure. The residue was completely dissolved in 100 mL of ethanol, which was then concentrated to 50 mL. Crystals formed in two hours, which were filtered, washed with ethanol and dried under reduced pressure to afford the pure title compound as a solid. $^1$H NMR (DMSO-d6, 500 MHz): δ (ppm) 8.65-8.58 (m, 1H), 4.28-4.09 (m, 1H), 4.00-3.80 (m, 2H), 3.63-3.56 (m, 1H), 3.43-3.35 (m, 3H), 3.20-3.14 (m, 1H), 3.12-3.02 (m, 1H), 1.84-1.54 (m, 4H); LCMS (ESI): m/z 288 [M+H]$^+$; 99%; RT=1.63 min; (AQUITY UPLC BEH C18 column, 0.1% FORMIC ACID in water with MeCN). Chiral purity by HPLC~99.7%; SFC METHOD: Column: CHIRALCEL OX-H (4.6*250) mm, 5 u, Co-solvent: 0.5% DEA in Methanol, Total flow: 4 g/mn, % Co-solvent: solvent: 40%, Temperature: 30° C., ABPR: 100 bar, RT: 1.83 min.

Preparations 10 to 16 were carried out in a similar manner to that used for Preparation 9. In some cases the crude product was purified further by column chromatography rather than recrystallisation. In cases where the initially isolated product is of lower than desired enantiomeric purity it can, if wished, be further purified by chiral SFC.

Preparation 10

3-((2-Chloro-5-oxido-6,7-dihydrothieno[3,2-d]pyrimidin-4-yl)amino)thietane-1,1-dioxide

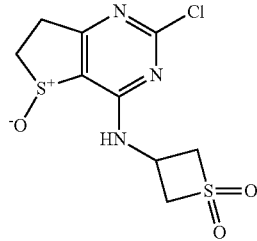

Isolated as a solid. $^1$H NMR (DMSO-d6, 500 MHz): δ (ppm) 9.43-9.38 (m, 1H), 4.75-4.68 (m, 1H), 4.63-4.50 (m, 2H), 4.45-4.30 (m, 2H), 3.69-3.62 (m, 1H), 3.49-3.41 (m, 1H), 3.26-3.19 (m, 1H), 3.13-3.09 (m, 1H); LCMS (ESI): m/z 308 [M+H]$^+$; 95.5%; RT=1.72 min; (AQUITY UPLC BEH C18 column, 0.1% FORMIC ACID in water with MeCN). Chiral purity by HPLC 49.4%; SFC METHOD: Column: CHIRALPAK AD-H (4.6*250) mm, 5 u, Co-solvent: 0.5% DEA in Methanol, Total flow: 4 g/mn, % Co-solvent: 50%, Temperature: 30° C., ABPR: 100 bar, RT: 1.52 min. No chiral purification was carried out at this stage.

Preparation 11

Methyl (3S)-3-(((5R)2-chloro-5-oxido-6,7-dihydrothieno[3,2-d]pyrimidin-4-yl)amino)pyrrolidine-1-carboxylate

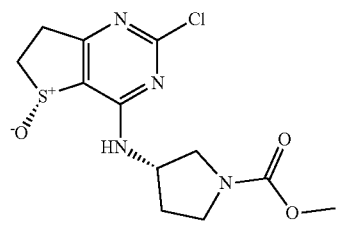

Isolated as a solid. $^1$H NMR (DMSO-d6, 400 MHz): δ (ppm) 8.95-8.90 (m, 1H), 4.68-4.60 (m, 1H), 3.67-3.57 (m, 5H), 3.48-3.35 (m, 3H), 3.32-3.26 (m, 1H), 3.23-3.13 (m, 1H), 3.12-3.04 (m, 1H), 2.18-2.11 (m, 1H), 2.02-1.95 (m, 1H). and Chiral purity by HPLC~92.7%; SFC METHOD: Column: Lux Amylose-2 (4.6*250) mm, 5 u, Co-solvent: 0.5% DEA in Methanol, Total flow: 4 g/mn, % Co-solvent: 40%, Temperature: 30° C., ABPR: 100 bar, RT: 2.63 min.

Preparation 12

Methyl (3R)-3-(((5R)2-chloro-5-oxido-6,7-dihydrothieno[3,2-d]pyrimidin-4-yl)amino)pyrrolidine-1-carboxylate

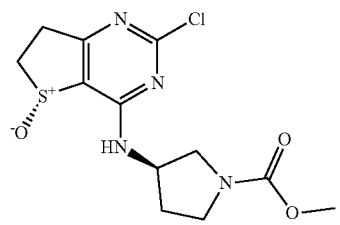

Isolated as a solid. $^1$H NMR (DMSO-d6, 400 MHz): δ (ppm) 8.96-8.90 (m, 1H), 4.62-4.55 (m, 1H), 3.71-3.53 (m, 5H), 3.46-3.34 (m, 3H), 3.21-3.14 (m, 1H), 3.23-3.11 (m, 1H), 3.10-3.02 (m, 1H), 2.20-2.12 (m, 1H), 2.04-1.91 (m, 1H); LCMS (ESI): m/z 331 [M+H]$^+$; 99%; RT=1.75 min; (AQUITY UPLC BEH C18 column, 0.1% FORMIC ACID in water with MeCN) and Chiral purity by HPLC~99.3%; SFC METHOD: Column: Lux Amylose-2 (4.6*250) mm, 5 u, Co-solvent: 0.5% DEA in Methanol, Total flow: 3 g/mn, % Co-solvent: 40%, Temperature: 30° C., ABPR: 100 bar, RT: 3.46 min.

Preparation 13

Methyl (3R)-3-(((5R)-2-chloro-5-oxido-6,7-dihydrothieno[3,2-d]pyrimidin-4-yl)amino)piperidine-1-carboxylate

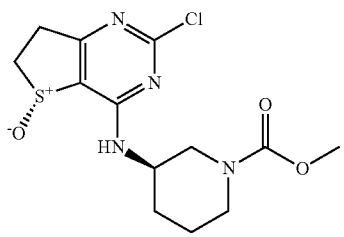

Isolated as a solid. $^1$H NMR (DMSO-d6, 500 MHz): δ (ppm) 8.60-8.52 (m, 1H), 4.08-4.02 (m, 2H), 3.90-3.86 (m, 1H), 3.64-3.56 (m, 4H), 3.45-3.38 (m, 1H), 3.20-3.15 (m, 1H), 3.10-3.01 (m, 1H), 2.80-2.75 (m, 2H), 1.95-1.89 (m, 1H), 1.80-1.68 (m, 1H), 1.65-1.59 (m, 1H), 1.50-1.39 (m, 1H); LCMS (ESI): m/z 345 [M+H]$^+$; 95%; RT=1.62 min; (AQUITY UPLC BEH C18 column, 0.1% FORMIC ACID in water with MeCN) and Chiral purity by HPLC~98.6%; SFC METHOD: Column: CHIRALPAK IE (4.6*250) mm, 5 u, Co-solvent: 0.5% DEA in Methanol, Total flow: 4 g/mn, % Co-solvent: 40%, Temperature: 30° C., ABPR: 100 bar, RT: 4.13 min.

Preparation 14

Methyl (3S)-3-(((5R)-2-chloro-5-oxido-6,7-dihydrothieno[3,2-d]pyrimidin-4-yl)amino)piperidine-1-carboxylate

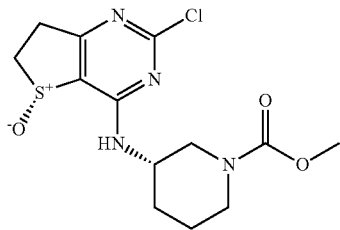

Isolated as a solid. $^1$H NMR (DMSO-d6, 400 MHz): δ (ppm) 8.64-8.59 (m, 1H), 4.09-4.01 (m, 2H), 3.91-3.86 (m, 1H), 3.65-3.55 (m, 4H), 3.50-3.33 (m, 1H), 3.21-3.02 (m, 1H), 2.87-2.71 (m, 2H), 1.92-1.88 (m, 1H), 1.76-1.68 (m, 1H), 1.77-1.67 (m, 1H), 1.65-1.55 (m, 1H), 1.49-1.35 (m, 1H); LCMS (ESI): m/z 345 [M+H]$^+$; 99%; RT=1.35 min; (AQUITY UPLC BEH C18 column, 0.1% FORMIC ACID in water with MeCN) and Chiral purity by HPLC~86.4%; SFC METHOD: Column(R,R) Whelk-01 (4.6*250) mm, 5 u, Co-solvent: 0.5% DEA in Methanol, Total flow: 4 g/mn, % Co-solvent: 40%, Temperature: 27.5° C., ABPR: 98 bar, RT: 3.17 min.

Preparation 15

(5R)-4-(Bicyclo[1.1.1]pentan-1-ylamino)-2-chloro-6,7-dihydrothieno[3,2-d]pyrimidine-5-oxide

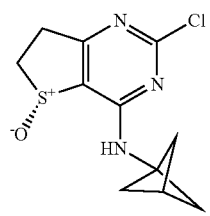

Isolated as a solid. $^1$H NMR (DMSO-d6, 300 MHz): δ (ppm) 9.34 (s, 1H), 3.67-3.48 (m, 1H), 3.41-3.33 (m, 1H), 3.24-3.09 (m, 1H), 3.07-2.92 (m, 1H), 2.52 (s, 1H), 2.14 (s, 6H); LCMS (ESI): m/z 270 [M+H]$^+$; 95.4%; RT=1.58 min; (AQUITY UPLC BEH C18 column, 0.1% FORMIC ACID in water with MeCN) and Chiral purity by HPLC~81.8%; SFC METHOD: Column: LUX AMYLOSEJ-2 (4.6*250) mm, 5 u, Co-solvent: 0.5% DEA in Methanol, Total flow: 3 g/mn, % Co-solvent: 20%, Temperature: 30° C., ABPR: 100 bar, RT: 3.63 min.

Preparation 16

(5R)-2-Chloro-4-((1-methylcyclobutyl)amino)-6,7-dihydrothieno[3,2-d]pyrimidine-5-oxide

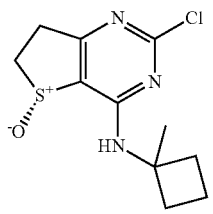

Isolated as a solid. $^1$H NMR (DMSO-d6, 400 MHz): δ (ppm) 8.79 (s, 1H), 3.61-3.50 (m, 1H), 3.43-3.35 (m, 1H), 3.19-3.08 (m, 1H), 3.04-2.97 (m, 1H), 2.38-2.24 (m, 2H), 2.11-2.01 (m, 2H), 1.88-1.73 (m, 2H), 1.50 (s, 3H); LCMS (ESI): m/z 272 [M+H]$^+$; 97.8%; RT=1.55 min; (AQUITY UPLC BEH C18 column, 0.1% FORMIC ACID in water with MeCN) and Chiral purity by HPLC~97.4%; SFC METHOD: Column: CHIRALCEL OD-H (4.6*250) mm, 5 u, Co-solvent: 0.5% DEA in Methanol, Total flow: 3 g/mn, % Co-solvent: 20%, Temperature: 30° C., ABPR: 100 bar, RT: 3.65 min.

Example 1

(R)-2-(3-Phenylazetidin-1-yl)-4-((tetrahydro-2H-pyran-4-yl)amino)-6,7-dihydrothieno[3,2-d]pyrimidine 5-oxide

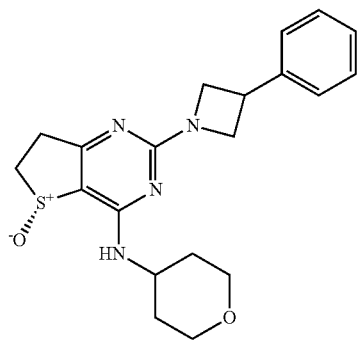

To a stirred solution of the compound of Preparation 9 (70 mg, 0.24 mmol) and 3-phenylazetidine (61 mg, 0.36 mmol) in NMP (2.5 mL) under $N_2$ was added DIPEA (0.12 mL, 0.729 mmol). The reaction was then heated for 16 hours at 100° C. in a sealed tube. The reaction was allowed to cool to room temperature, then poured into ice cold water. The organic portion was extracted with EtOAc, washed with water, dried over $Na_2SO_4$ and concentrated under reduced pressure to afford the crude compound. Purification by flash chromatography, using 1-6% MeOH/DCM as eluent, gave the title compound. $^1$H NMR (DMSO-d6, 500 MHz): δ (ppm) 7.60 (d, J=7.6 Hz, 1H), 7.40-7.34 (m, 4H), 7.28-7.22 (m, 1H), 4.50-4.42 (m, 2H), 4.22-4.15 (m, 1H), 4.04-3.97 (m, 2H), 3.96-3.83 (m, 3H), 3.47-3.34 (m, 3H), 3.25-3.19 (m, 1H), 3.00-2.84 (m, 2H), 1.82-1.75 (m, 2H), 1.71-1.59 (m, 2H); LCMS (ESI): m/z 385 [M+H]$^+$; 99.4%; RT=1.73 min; (AQUITY UPLC BEH C18 column, 0.1% FORMIC ACID in water with MeCN) and chiral purity by HPLC, 94.8% SFC METHOD: Column: Chiralcel OJ-H (4.6*250) mm, 5 u, Co-solvent: 0.5% DEA in Methanol, Total flow: 4 g/mn, % Co-solvent: 40%, Temperature: 30° C., ABPR: 100 bar, RT: 1.72 min.

Example 2

(R)-2-(3-Phenoxyazetidin-1-yl)-4-((tetrahydro-2H-pyran-4-yl)amino)-6,7-dihydrothieno[3,2-d]pyrimidine 5-oxide

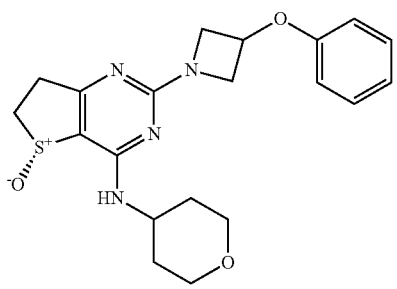

According to the method of Example 1, the compound of Preparation 9 was reacted with 3-phenoxyazetidine to give the title compound as a solid. $^1$H NMR (DMSO-d6, 300 MHz): δ (ppm) 7.71-7.62 (m, 1H), 7.33 (t, J=8.0 Hz, 2H), 6.99 (t, J=7.3 Hz, 1H), 6.88 (d, J=7.9 Hz, 2H), 5.18-5.11 (m, 1H), 4.54-4.45 (m, 2H), 4.24-4.13 (m, 1H), 3.99-3.82 (m, 4H), 3.49-3.35 (m, 2H), 3.15-3.20 (m, 2H), 3.02-2.83 (m, 2H), 1.81-1.70 (m, 2H), 1.68-1.52 (m, 2H); LCMS (ESI): m/z 401 [M+H]$^+$; 99.8%; RT=1.65 min; (AQUITY UPLC BEH C18 column, 0.1% FORMIC ACID in water with MeCN) and Chiral purity by HPLC~97.9%; SFC METHOD: Column: Chiralcel OJ-H (4.6*250) mm, 5 u, Co-solvent: 0.5% DEA in Methanol, Total flow: 3 g/mn, % Co-solvent: 20%, Temperature: 30° C., Back Pressure: 100 bar, RT: 4.5 min.

Example 3

(R)-2-(3-(4-Fluorophenoxy)azetidin-1-yl)-4-((tetrahydro-2H-pyran-4-yl)amino)-6,7-dihydrothieno[3,2-d]pyrimidine 5-oxide

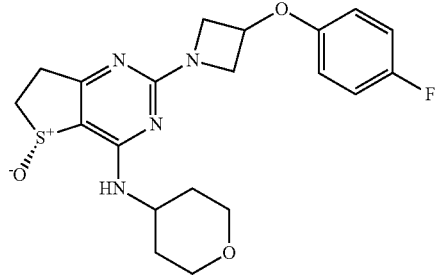

According to the method of Example 1, the compound of Preparation 9 was reacted with 3-(4-fluorophenoxy)azetidine to give the title compound as a solid. $^1$H NMR (DMSO-d6, 500 MHz): δ (ppm) 7.69-7.62 (m, 1H), 7.22-7.13 (m, 2H), 6.93-6.88 (m, 2H), 5.12-5.06 (m, 1H), 4.51-4.45 (m, 2H), 4.22-4.14 (m, 1H), 3.98-3.91 (m, 2H), 3.90-3.83 (m, 2H), 3.46-3.34 (m, 3H), 3.25-3.16 (m, 1H), 3.00-2.86 (m, 2H), 1.80-1.72 (m, 2H), 1.68-1.59 (m, 2H); LCMS (ESI): m/z 419 [M+H]$^+$; 99.2%; RT=1.5 min; (AQUITY UPLC BEH C18 column, 0.1% FORMIC ACID in water with MeCN) and Chiral purity by HPLC~99.4%; SFC METHOD: Column: CHIRALCEL OX-H (4.6*250) mm, 5 u, Co-Solvent: 0.5% DEA in Methanol, Temperature: 30° C., Flow: 4 g/mn, Pressure: 100 bar, RT: 6.37 min.

Example 4

(R)-3-((5-Oxido-2-(3-phenylazetidin-1-yl)-6,7-dihydrothieno[3,2-d]pyrimidin-4-yl)amino)thietane 1,1-dioxide

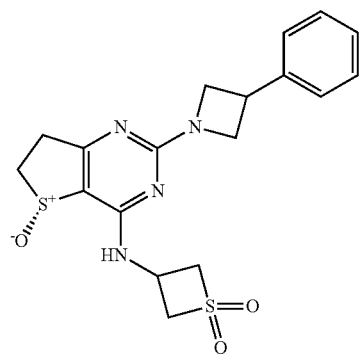

According to the method of Example 1, the compound of Preparation 10 was reacted with 3-phenylazetidine to give the title compound as a solid. Further purification by chiral SFC using a Whelk (R,R) column and using 50% methanol as co-solvent gave the title compound. $^1$H NMR (CD$_3$OD, 500 MHz): δ (ppm) 7.42-7.33 (m, 4H), 7.28-7.21 (m, 1H), 4.61-4.50 (m, 4H), 4.39-4.29 (m, 2H), 4.25-4.13 (m, 2H), 4.00-3.94 (m, 1H), 3.66-3.58 (m, 1H), 3.45-3.36 (m, 2H), 3.17-3.09 (m, 2H); LCMS (ESI): m/z 405 [M+H]$^+$; 98.8%; RT=2.16 min; (AQUITY UPLC BEH C18 column, 0.1% formic acid in water with MeCN) and Chiral purity by HPLC~99%; SFC; METHOD: Co-solvent: 0.5% DEA in Methanol, Column: (R,R)WHELK-01 (4.6*250) mm, 5 u, Temperature: 23.5° C., Flow: 4 g/mn, Pressure: 100 bar, RT: 6.00 min.

Example 5

Methyl (3S)-3-(((5R)-5-oxido-2-(3-phenylazetidin-1-yl)-6,7-dihydrothieno[3,2-d]pyrimidin-4-yl)amino)pyrrolidine-1-carboxylate

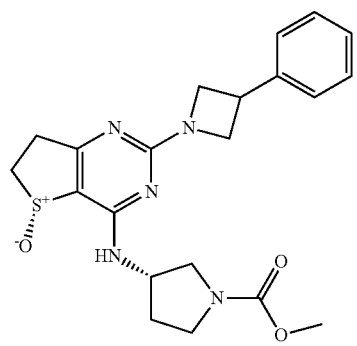

According to the method of Example 1, the compound of Preparation 11 was reacted with 3-phenylazetidine to give the title compound as a solid. $^1$H NMR (DMSO-d6, 500 MHz): δ (ppm) 8.00-7.92 (m, 1H), 7.40-7.33 (m, 4H), 7.29-7.23 (m, 1H), 4.62-4.55 (m, 1H), 4.49-4.43 (m, 2H), 4.11-3.98 (m, 2H), 3.97-3.89 (m, 1H), 3.72-3.60 (m, 1H), 3.57 (d, J=2.9 Hz, 3H), 3.49-3.40 (m, 2H), 3.30-3.17 (m, 3H), 3.02-2.87 (m, 2H), 2.15-1.95 (m, 2H); LCMS (ESI): m/z 428 [M+H]$^+$; 99.4%; RT=1.49 min; (AQUITY UPLC BEH C18 column, 0.1% FORMIC ACID in water with MeCN) and Chiral purity by HPLC~99.7%; SFC METHOD: Column: Chiralcel OD-H (4.6*250) mm, 5 u, Co-solvent: 0.5% DEA in Methanol, Total flow: 4 g/mn, % Co-solvent: 40%, Temperature: 30° C., ABPR: 100 bar, RT: 3.61 min.

Example 6

Methyl (3R)-3-(((5R)-5-Oxido-2-(3-phenylazetidin-1-yl)-6,7-dihydrothieno[3,2-d]pyrimidin-4-yl)amino)pyrrolidine-1-carboxylate

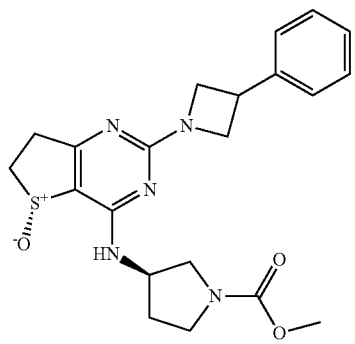

According to the method of Example 1, the compound of Preparation 12 was reacted with 3-phenylazetidine to give the title compound as a solid. $^1$H NMR (DMSO-d6, 500 MHz): δ (ppm) 8.01-7.90 (m, 1H), 7.40-7.33 (m, 4H), 7.28-7.24 (m, 1H), 4.61-4.52 (m, 1H), 4.50-4.45 (m, 2H), 4.10-3.98 (m, 2H), 3.98-3.91 (m, 1H), 3.63-3.55 (m, 4H), 3.48-3.39 (m, 2H), 3.31-3.15 (m, 3H), 3.02-2.96 (m, 17.2 Hz, 1H), 2.95-2.89 (m, 1H), 2.17-1.97 (m, 2H); LCMS (ESI): m/z 428 [M+H]$^+$; 99.6%; RT=1.74 min; (AQUITY UPLC BEH C18 column, 0.1% FORMIC ACID in water with MeCN) and Chiral purity by HPLC~99%; SFC METHOD: Co-solvent: 0.5% DEA in Methanol, column: Chiralcel OJ-H (4.6*250) mm, 5 u, Flow: 4 g/mn, Pressure: 100 bar, RT: 1.71 min.

Example 7

Methyl (3R)-3-(((5R)-2-(3-(4-Fluorophenoxy)azetidin-1-yl)-5-oxido-6,7-dihydrothieno[3,2-d]pyrimidin-4-yl)amino)piperidine-1-carboxylate

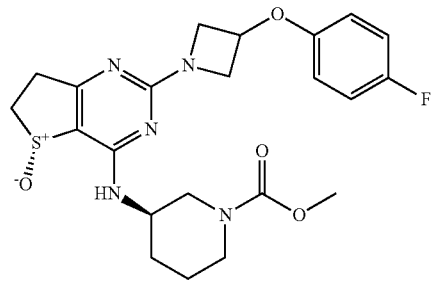

According to the method of Example 1, the compound of Preparation 13 was reacted with 3-(4-fluorophenoxy)azetidine to give the title compound as a solid. ¹H NMR (DMSO-d6, 500 MHz): δ (ppm) 7.70-7.61 (m, 1H), 7.25-7.07 (m, 2H), 6.99-6.88 (m, 2H), 5.13-5.09 (m, 1H), 4.52-4.46 (m, 2H), 4.29-4.22 (m, 1H), 3.98-3.88 (m, 4H), 3.66-3.38 (m, 4H), 3.38-3.19 (m, 1H), 3.01-2.84 (m, 2H), 2.79-2.54 (m, 2H), 1.92-1.84 (m, 1H), 1.74-1.56 (m, 2H), 1.46-1.35 (m, 1H); LCMS (ESI): m/z 476 [M+H]⁺; 99.4%; RT=2.00 min; (AQUITY UPLC BEH C18 column, 0.1% FORMIC ACID in water with MeCN) and Chiral purity by HPLC~99%; SFC METHOD: Co-solvent: 0.5% DEA in Methanol, column: LuxCellulose-2 (4.6*250) mm, 5 u, Flow: 4 g/mn, Back Pressure: 100 bar, RT: 5.85 min.

Example 8

Methyl (3S)-3-(((5R)-2-(3-(4-Fluorophenoxy)azetidin-1-yl)-5-oxido-6,7-dihydrothieno[3,2-d]pyrimidin-4-yl)amino)piperidine-1-carboxylate

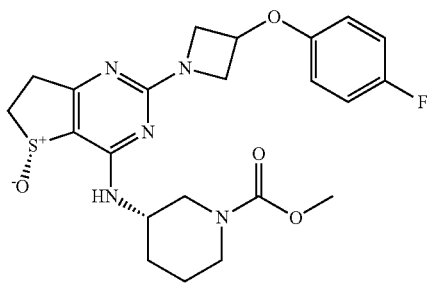

According to the method of Example 1, the compound of Preparation 14 was reacted with 3-(4-fluorophenoxy)azetidine to give the title compound as a solid. ¹H NMR (DMSO-d6, 500 MHz): δ (ppm) 7.70-7.61 (m, 1H), 7.25-7.07 (m, 2H), 6.99-6.88 (m, 2H), 5.13-5.09 (m, 1H), 4.52-4.46 (m, 2H), 4.29-4.22 (m, 1H), 3.98-3.88 (m, 4H), 3.66-3.38 (m, 4H), 3.38-3.19 (m, 1H), 3.01-2.84 (m, 2H), 2.79-2.54 (m, 2H), 1.92-1.84 (m, 1H), 1.74-1.56 (m, 2H), 1.46-1.35 (m, 1H); LCMS (ESI): m/z 476 [M+H]⁺; 99.4%; RT=2.00 min; (AQUITY UPLC BEH C18 column, 0.1% FORMIC ACID in water with MeCN) and Chiral purity by HPLC~99%; SFC METHOD: C0-solvent: 0.5% DEA in Methanol, column: LuxCellulose-2 (4.6*250) mm, 5 u, Flow: 4 g/mn, Back Pressure: 100 bar, RT: 5.85 min.

Example 9

(R)-4-(Bicyclo[1.1.1]pentan-1-ylamino)-2-(3-(4-fluorophenyl)azetidin-1-yl)-6,7-dihydrothieno[3,2-d]pyrimidine 5-oxide

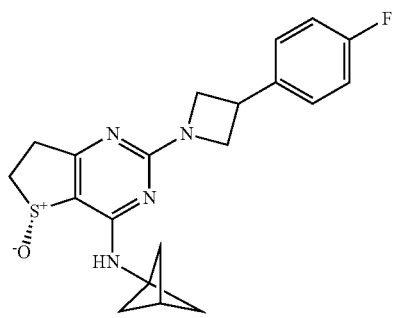

According to the method of Example 1, the compound of Preparation 15 was reacted with 3-(4-fluorophenyl)azetidine to give the title compound of ~81% chiral purity. Further purification by chiral SFC gave the title compound as a solid. ¹H NMR (DMSO-d6, 500 MHz): δ (ppm) 8.37 (s, 1H), 7.50-7.42 (m, 2H), 7.18 (t, J=8.9 Hz, 2H), 4.49-4.41 (m, 2H), 4.04-3.92 (m, 3H), 3.47-3.37 (m, 1H), 3.24-3.16 (m, 1H), 3.00-2.92 (m, 1H), 2.89-2.84 (m, 1H), 2.44 (s, 1H), 2.12 (s, 6H)); LCMS (ESI): m/z 385 [M+H]⁺; 98.5%; RT=1.93 min; (AQUITY UPLC BEH C18 column, 0.1° % FORMIC ACID in water with MeCN) and Chiral purity by HPLC~99.8%; SFC METHOD: Column: Chiralpak AD-H (4.6*250) mm, 5 u, Co-solvent: 0.5% DEA in Methanol, Total flow: 4 g/mn, % Co-solvent: 40%, Temperature: 30° C., ABPR: 100 bar, RT: 2.26 min.

Example 10

(R)-4-(Bicyclo[1.1.1]pentan-1-ylamino)-2-(3-(4-fluorophenoxy)azetidin-1-yl)-6,7-dihydrothieno[3,2-d]pyrimidine 5-oxide

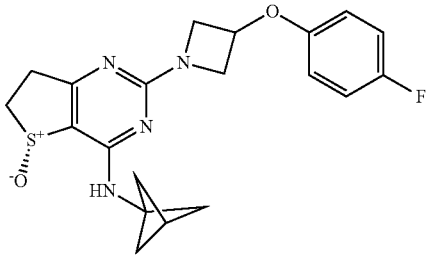

According to the method of Example 1, the compound of Preparation 15 was reacted with 3-(4-fluorophenoxy)azetidine to give the title compound of ~81% chiral purity. Further purification by chiral SFC using a Chiralpak IA column and methanol as co-solvent gave the title compound as a solid. ¹H NMR (DMSO-d6, 500 MHz): δ (ppm) 8.41 (s, 1H), 7.20-7.12 (m, 2H), 6.97-6.81 (m, 2H), 5.14-5.06 (m, 1H), 4.58-4.49 (m, 2H), 4.03-3.92 (m, 2H), 3.47-3.37 (m, 1H), 3.25-3.16 (m, 1H), 2.99-2.92 (m, 1H), 2.90-2.80 (m, 1H), 2.45 (s, 1H), 2.11 (s, 6H); LCMS (ESI): m/z 401 [M+H]⁺; 97.6%; RT=1.80 min; (AQUITY UPLC BEH C18 column, 0.1% FORMIC ACID in water with MeCN) and Chiral purity by HPLC~99%; SFC METHOD: Column: Chiralpak AD-H (4.6*250) mm, 5 u, Co-solvent: Methanol, Total flow: 4 g/mn, % Co-solvent: 40%, Temperature: 30° C., ABPR: 100 bar, RT: 3.1 min.

Example 11

(R)-4-(Bicyclo[1.1.1]pentan-1-ylamino)-2-(3-phenylazetidin-1-yl)-6,7-dihydrothieno[3,2-d]pyrimidine 5-oxide

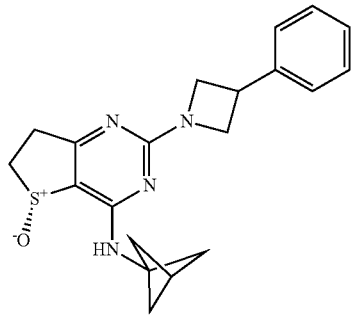

According to the method of Example 1, the compound of Preparation 15 was reacted with 3-phenylazetidine to give the title compound of ~81% chiral purity. Further purification by chiral SFC gave the title compound as a solid. $^1$H NMR (DMSO-d6, 400 MHz): δ (ppm) 8.37 (s, 1H), 7.43-7.30 (m, 4H), 7.31-7.24 (m, 1H), 4.51-4.42 (m, 2H), 4.07-3.89 (m, 3H), 3.47-3.38 (m, 1H), 3.21-3.15 (m, 1H), 3.01-2.94 (m, 1H), 2.92-2.85 (m, 1H), 2.44 (s, 1H), 2.12 (s, 6H); LCMS (ESI): m/z 367 [M+H]$^+$; 99%; RT=2.2 min; (AQUITY UPLC BEH C18 column, 0.1% FORMIC ACID in water with MeCN).

Example 12

(R)-4-(Bicyclo[1.1.1]pentan-1-ylamino)-2-(3-(pyridin-2-yl)azetidin-1-yl)-6,7-dihydrothieno[3,2-d]pyrimidine 5-oxide

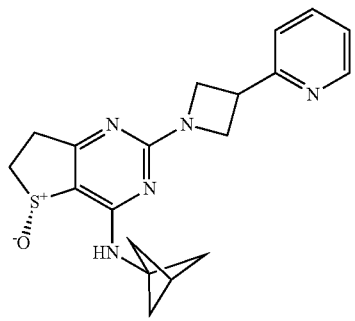

According to the method of Example 1, the compound of Preparation 15 was reacted with 2-(azetidin-3-yl)pyridine to give the title compound of ~81% chiral purity. Further purification by chiral SFC gave the title compound as a solid. $^1$H NMR (DMSO d6, 500 MHz): δ (ppm) 8.65-8.56 (m, 1H), 8.35 (s, 1H), 7.65-7.74 (m, 1H), 7.78-7.73 (m, 1H), 7.37 (d, J=7.9 Hz, 1H), 7.36-7.24 (m, 1H), 4.43-4.38 (m, 2H), 4.19 (m, 2H), 4.12-4.04 (m, 1H), 3.45-3.38 (m, 1H), 3.31-3.12 (m, 1H), 2.95-2.90 (m, 1H), 2.90-2.84 (m, 1H), 2.43 (s, 1H), 2.11 (s, 6H); LCMS (ESI): m/z 368 [M+H]$^+$; 98.2%; RT=1.52 min; (AQUITY UPLC BEH C18 column, 0.1% FORMIC ACID in water with MeCN) and Chiral purity by HPLC~96%; SFC METHOD: Column: (R,R) WHELK-01 (4.6*250) mm, 5 u, Co-solvent: 0.5% DEA in Methanol, Total flow: 4 g/mn, % Co-solvent: 40%, Temperature: 30° C., ABPR: 100 bar, RT: 3.63 min.

Example 13

(R)-4-(Bicyclo[1.1.1]pentan-1-ylamino)-2-(3-(3-fluorophenyl)azetidin-1-yl)-6,7-dihydrothieno[3,2-d]pyrimidine 5-oxide

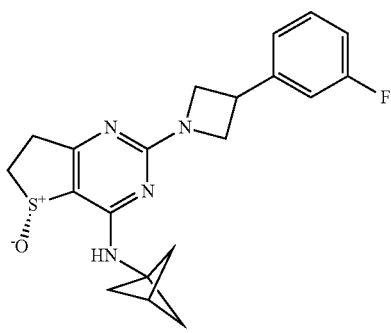

According to the method of Example 1, the compound of Preparation 15 was reacted with 3-(3-fluorophenyl)azetidine to give the title compound of ~81% chiral purity. Further purification by chiral SFC gave the title compound as a solid. $^1$H NMR (DMSO-d6, 500 MHz): δ (ppm) 8.37 (s, 1H), 7.42-7.37 (m, 1H), 7.30-7.26 (m, 2H), 7.11-7.02 (m, 1H), 4.51-4.39 (m, 2H), 4.07-3.95 (m, 3H), 3.45-3.38 (m, 1H), 3.21-3.11 (m, 1H), 3.01-2.98 (m, 1H), 2.97-2.89 (m, 1H), 2.44 (s, 1H), 2.12 (s, 6H); LCMS (ESI): m/z 385 [M+H]$^+$; 99.5%; RT=1.93 min; (AQUITY UPLC BEH C18 column, 0.1% FORMIC ACID in water with MeCN) and Chiral purity by HPLC~96.2%; SFC METHOD: Column: Chiralpak AD-H (4.6*250) mm, 5 u, Co-solvent: 0.5% DEA in Methanol, Total flow: 4 g/mn, % Co-solvent: 40%, Temperature: 30° C., ABPR: 100 bar, RT: 4.05 min.

Example 14

(R)-4-(Bicyclo[1.1.1]pentan-1-ylamino)-2-(3-(pyridin-3-yloxy)azetidin-1-yl)-6,7-dihydrothieno[3,2-d]pyrimidine 5-oxide

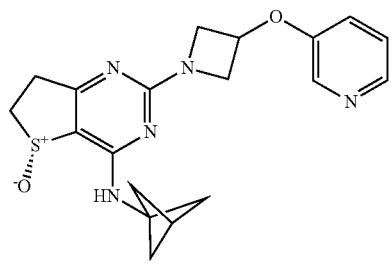

According to the method of Example 1, the compound of Preparation 15 was reacted with 3-(azetidin-3-yloxy)pyridine to give the title compound of ~81% chiral purity. Further purification by chiral SFC gave the title compound as a solid. $^1$H NMR (DMSO-d6, 400 MHz): δ (ppm) 8.42 (s, 1H), 8.31-8.24 (m, 2H), 7.42-7.31 (m, 2H), 5.25-5.20 (m, 1H), 4.60-4.52 (m, 2H), 4.04-3.96 (m, 2H), 3.48-3.40 (m, 1H), 3.28-3.18 (m, 1H), 3.02-2.83 (m, 2H), 2.45 (s, 1H), 2.11 (s, 6H)); LCMS (ESI): m/z 384 [M+H]$^+$; 98.6%; RT=1.18 min; (AQUITY UPLC BEH C18 column, 0.1% FORMIC ACID in water with MeCN) and Chiral purity by HPLC~97.5%; SFC METHOD: Column: Chiralpak AD-H (4.6*250) mm, 5 u, Co-solvent: 0.5% DEA in Methanol, Total flow: 4 g/mn, % Co-solvent: 40%, Temperature: 30° C., ABPR: 100 bar, RT: 3.48 min.

Example 15

(R)-4-((1-Methylcyclobutyl)amino)-2-(3-(pyridin-2-yl)azetidin-1-yl)-6,7-dihydrothieno[3,2-d]pyrimidine 5-oxide

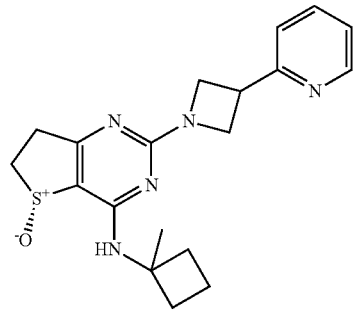

According to the method of Example 1, the compound of Preparation 16 was reacted with 2-(azetidin-3-yl)pyridine to give the title compound as a solid. $^1$H NMR (DMSO-d6, 400 MHz): δ (ppm) 8.65-8.58 (m, 1H), 7.85-7.72 (m, 1H), 7.68 (s, 1H), 7.36 (d, J=7.8 Hz, 1H), 7.31-7.25 (m, 1H), 4.43-4.29 (m, 2H), 4.22-4.10 (m, 2H), 4.09-4.02 (m, 1H), 3.45-3.39 (m, 1H), 3.22-3.18 (m, 1H), 2.98-2.82 (m, 2H), 2.41-2.24 (m, 2H), 2.12-1.95 (m, 2H), 1.83-1.71 (m, 2H), 1.51 (s, 3H); LCMS (ESI): m/z 370 [M+H]$^+$; 99.2%; RT=1.20 min; (AQUITY UPLC BEH C18 column, 0.1% FORMIC ACID in water with MeCN) and Chiral purity by HPLC~87.3%; SFC METHOD: Column: Chiralpak AD-H (4.6*250) mm, 5 u, Co-solvent: 0.5% DEA in Methanol, Total flow: 4 g/mn, % Co-solvent: 40%, Temperature: 30° C., ABPR: 100 bar, RT: 1.97 min.

Example 16

(R)-4-((1-Methylcyclobutyl)amino)-2-(3-(pyridin-3-yl)azetidin-1-yl)-6,7-dihydrothieno[3,2-d]pyrimidine 5-oxide

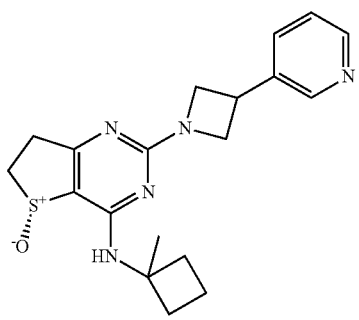

According to the method of Example 1, the compound of Preparation 16 was reacted with 3-(azetidin-3-yl)pyridine to give the title compound as a solid. $^1$H NMR (DMSO-d6, 500 MHz): δ (ppm) 8.56 (d, J=1.8 Hz, 1H), 8.50-8.44 (m, 1H), 7.90-7.84 (m, 1H), 7.72 (s, 1H), 7.49-7.38 (m, 1H), 4.47-4.40 (m, 2H), 3.99 (br s, 3H), 3.45-3.36 (m, 1H), 3.35-3.20 (m, 1H), 2.99-2.91 (m, 1H), 2.89-2.82 (m, 1H), 2.40-2.26 (m, 2H), 2.05-1.98 (m, 2H), 1.83-1.71 (m, 2H), 1.51 (s, 3H)); LCMS (ESI): m/z 370 [M+H]$^+$; 99.2%; RT=1.56 min; (AQUITY UPLC BEH C18 column, 0.1% FORMIC ACID in water with MeCN) and Chiral purity by HPLC~99.2%; SFC METHOD: Column: Chiralpak AD-H (4.6*250) mm, 5 u, Co-solvent: 0.5% DEA in Methanol, Total flow: 4 g/mn, % Co-solvent: 40%, Temperature: 30° C., ABPR: 100 bar, RT: 1.91 min.

Example 17

(5R)—N-(1,1-Dioxothian-4-yl)-5-oxido-2-(3-phenylazetidin-1-yl)-6,7-dihydrothieno[3,2-d]pyrimidin-4-yl-amine

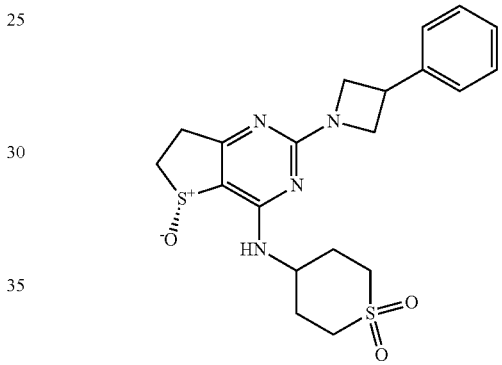

The title compound was prepared according to the methods of Preparation 1, Preparation 9 and Example 1, starting from 2,4-dichloro-6,7-dihydrothieno[3,2-d]pyrimidine, 1,1-dioxothian-4-amine and 3-phenylazetidine. The title compound was isolated as a solid. $^1$H NMR (DMSO-d6, 500 MHz): δ (ppm) 8.00-7.92 (m, 1H), 7.40-7.33 (m, 3H), 7.29-7.23 (m, 1H), 4.62-4.55 (m, 1H), 4.49-4.43 (m, 2H), 4.11-3.98 (m, 2H), 3.97-3.89 (m, 1H), 3.72-3.60 (m, 1H), 3.57 (d, J=2.9 Hz, 3H), 3.49-3.40 (m, 2H), 3.30-3.17 (m, 3H), 3.02-2.87 (m, 2H), 2.15-1.95 (m, 2H); LCMS (ESI): m/z 428 [M+H]$^+$; 99.4%; RT=1.49 min; (AQUITY UPLC BEH C18 column, 0.1% FORMIC ACID in water with MeCN) and Chiral purity by HPLC~99.7%; SFC METHOD: Column: Chiralcel OD-H (4.6*250) mm, 5 u, Co-solvent: 0.5% DEA in Methanol, Total flow: 4 g/mn, % Co-solvent: 40%, Temperature: 30° C., ABPR: 100 bar, RT: 3.61 min.

PDE4 Assay

The human PDE4D catalytic domain (UniProt no. Q08499 [5380-L740]) was incubated with a mixture of non-labelled cAMP (cyclic adenosine monophosphate) and fluorescein amidite (FAM) conjugated cAMP and titrated test or reference compound. Following brief incubation the enzymatic reaction was stopped by addition of binding buffer containing nanoparticles with immobilized trivalent metal ions capable of binding 1) AMP phospho groups and 2) terbium (Tb) donor fluorophores. Subsequent excitation of the Tb donor triggers time-resolved FRET to adjacent FAM acceptor molecules resulting in light emission. In the presence of a PDE4 inhibitor, AMP generation was reduced resulting in a lower fluorescence signal. The cAMP phosphodiester is not bound by the detection system.

The results were calculated as the molar concentrations resulting in 50% inhibition of the substrate cleavage compared to controls samples, and are expressed as $IC_{50}$ (nM).

PDE4 $IC_{50}$ Ranges:

* indicates that $IC_{50}$ values are >50 nM and <150 nM
** indicates that $IC_{50}$ values are >10 and <50 nM
*** indicates that $IC_{50}$ values are <10 nM TNF-α Release Human peripheral blood mononuclear cells (PBMC) were isolated from buffy coats. The blood is mixed with saline at a ratio of 1:1, and the PBMC were isolated using Lymphoprep Tubes™ (Nycomed, Norway). The PBMC were suspended in RPMI1640 with 0.5% human serum albumin, pen/strep and 2 mM L-glutamine at a concentration of 5×105 c/ml. The cells were pre-incubated for 30 minutes with the test compounds in 96 well tissue culture plates and stimulated for 18 hours with lipopolysaccharide 1 mg/ml (Sigma). TNF-α concentration in the supernatants was measured using homogeneous time-resolved fluorescence resonance (TR-FRET). The assay is quantified by measuring fluorescence at 665 nm (proportional to TNF-α concentration) and 620 nm (control).

Results were expressed as $IC_{50}$ values calculated from inhibition curves using as positive controls the secretion in LPS stimulated wells and as negative controls the secretion in unstimulated cells.

TNF-α $IC_{50}$ Ranges:

* indicates that $IC_{50}$ values are >50 and <150 nM
** indicates that $IC_{50}$ values are >10 and <50 nM
*** indicates that $IC_{50}$ values are <10 nM The results are shown in Table 1 below.

TABLE 1

| Example | PDE4 $IC_{50}$ range | TNF-α $IC_{50}$ range |
|---|---|---|
| 1 | *** | *** |
| 2 | *** | *** |
| 3 | *** | *** |
| 4 |  | ** |
| 5 | ** | ** |
| 6 | *** | *** |
| 7 | *** | *** |
| 8 | *** | *** |
| 9 | *** | *** |
| 10 | *** | *** |
| 11 | *** | *** |
| 12 | ** | ** |
| 13 | *** | *** |
| 14 | *** | ** |
| 15 | *** | *** |
| 16 | ** | ** |
| 17 | *** | *** |

CLAUSES

In view of the description the present inventors have in particular provided:

Clause 1. A compound of general formula (I)

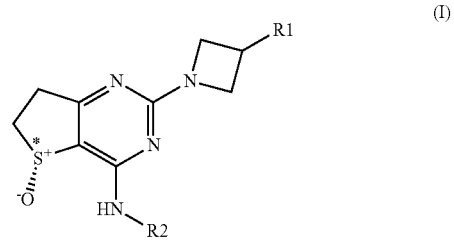

wherein $R^1$ is selected from the group consisting of phenyl, 6 membered heteroaryl, phenoxy and 6 membered heteroaryloxy; all of which are optionally substituted with one or more substituents independently selected from $R^3$; and $R^2$ is selected from the group consisting of $(C_3-C_7)$ cycloalkyl, bridged $(C_3-C_7)$cycloalkyl and (4-7 membered) heterocycloalkyl; all of which are optionally substituted with one or more substituents independently selected from $R^4$; and $R^3$ is selected from the group consisting of halogen, —CN, $(C_1-C_4)$alkyl, halo$(C_1-C_4)$alkyl, hydroxy$(C_1-C_4)$alkyl and $(C_3-C_6)$cycloalkyl; and $R^4$ is selected from the group consisting of fluoro, —CN, —OH, $(C_1-C_4)$alkyl, halo$(C_1-C_4)$alkyl, hydroxy$(C_1-C_4)$alkyl, —$OR^x$, —$S(O)_2R^x$, —$S(O)_2NR^aR^b$, —$C(O)R^x$, —$C(O)(OR^x)$, and —$C(O)NR^aR^b$; and $R^x$ is selected from the group consisting of $(C_1-C_4)$alkyl and $(C_3-C_6)$cycloalkyl; and $R^a$ and $R^b$ are independently selected from the group consisting of hydrogen, $(C_1-C_4)$alkyl and $(C_3-C_6)$cycloalkyl; and S* represents a chiral sulfur atom with (R) stereochemistry; and pharmaceutically acceptable salts, enantiomers, mixtures of enantiomers, diastereomers, mixtures of diastereomers, hydrates and solvates thereof.

Clause 2. A compound according to clause 1, wherein $R^1$ is phenyl.

Clause 3. A compound according to clause 1, wherein $R^1$ is phenyl substituted with one of $R^3$.

Clause 4. A compound according to clause 3, wherein $R^3$ is halogen or $(C_1-C_4)$alkyl.

Clause 5. A compound according to clause 1, wherein $R^1$ is a 6 membered heteroaryl.

Clause 6. A compound according to clause 5, wherein $R^1$ is pyridinyl.

Clause 7. A compound according to clause 1, wherein $R^1$ is phenoxy.

Clause 8. A compound according to clause 1, wherein $R^1$ is phenoxy substituted with one of $R^3$.

Clause 9. A compound according to clause 8, wherein $R^3$ is halogen.

Clause 10. A compound according to clause 8 or 9, wherein $R^1$ is phenoxy substituted with fluoro.

Clause 11. A compound according to clause 1, wherein $R^1$ is a 6 membered heteroaryloxy, e.g. pyridyloxy.

Clause 12. A compound according to any one of the clauses 1-11, wherein $R^2$ is $(C_3-C_7)$cycloalkyl, optionally substituted with one or more substituents independently selected from $R^4$.

Clause 13. A compound according to clause 12, wherein $R^2$ is cyclobutyl, substituted with methyl.

Clause 14. A compound according to any one of the clauses 1-11, wherein $R^2$ is bridged $(C_3-C_7)$cycloalkyl, optionally substituted with one of $R^4$.

Clause 15. A compound according to clause 14, wherein $R^2$ is bicyclo[1.1.1]pentyl.

Clause 16. A compound according to any one of the clauses 1-11, wherein $R^2$ is (4-7) membered heterocycloalkyl, optionally substituted with one or more substituents independently selected from $R^4$.

Clause 17. A compound according to clause 16, wherein $R^2$ is (4-6) membered heterocycloalkyl, optionally substituted with —C(O)(OR$^x$), and R$^x$ is $(C_1-C_4)$alkyl.

Clause 18. A compound according to clause 17, wherein $R^2$ is piperidinyl or pyrrolidinyl, substituted with —C(O)(OR$^x$), and R$^x$ is $(C_1-C_4)$alkyl.

Clause 19. A compound according to clause 17, wherein $R^2$ is tetrahydropyranyl.

Clause 20. A compound according to clause 17, wherein $R^2$ is dioxothietanyl or dioxothianyl.

Clause 21. A compound according to any one of the clauses 1-20, wherein $R^1$ is phenyl which is optionally substituted with one or more substituents independently selected from $R^3$; and $R^2$ is selected from the group consisting of $(C_3-C_7)$cycloalkyl, bridged $(C_3-C_7)$cycloalkyl and (4-7 membered) heterocycloalkyl; all of which are optionally substituted with one or more substituents independently selected from $R^4$; or pharmaceutically acceptable salts, enantiomers, mixtures of enantiomers, diastereomers, mixtures of diastereomers, hydrates and solvates thereof.

Clause 22. A compound according to clause 21, wherein $R^1$ is phenyl, which is optionally substituted with one of $R^3$; and $R^2$ is (4-6 membered) heterocycloalkyl which is optionally substituted with one of $R^4$; or pharmaceutically acceptable salts, enantiomers, mixtures of enantiomers, diastereomers, mixtures of diastereomers, hydrates and solvates thereof.

Clause 23. A compound according to clause 21, wherein $R^1$ is phenyl which is optionally substituted with one of $R^3$; and $R^2$ is bridged $(C_3-C_7)$cycloalkyl; or pharmaceutically acceptable salts, enantiomers, mixtures of enantiomers, diastereomers, mixtures of diastereomers, hydrates and solvates thereof.

Clause 24. A compound according to any one of the clauses 1-20, wherein $R^1$ is phenoxy which is optionally substituted with one or more substituents independently selected from $R^3$; and $R^2$ is selected from the group consisting of $(C_3-C_7)$cycloalkyl, bridged $(C_3-C_7)$cycloalkyl and (4-7 membered) heterocycloalkyl; all of which are optionally substituted with one or more substituents independently selected from $R^4$; or pharmaceutically acceptable salts, enantiomers, mixtures of enantiomers, diastereomers, mixtures of diastereomers, hydrates and solvates thereof.

Clause 25. A compound according to clause 24, wherein $R^1$ is phenoxy, which is optionally substituted with halogen; and $R^2$ is (4-6 membered) heterocycloalkyl which is optionally substituted with one of $R^4$; or pharmaceutically acceptable salts, enantiomers, mixtures of enantiomers, diastereomers, mixtures of diastereomers, hydrates and solvates thereof.

Clause 26. A compound according to any one of the clauses 1-20, wherein $R^1$ is 6 membered heteroaryl which is optionally substituted with one or more substituents independently selected from $R^3$; and $R^2$ is selected from the group consisting of $(C_3-C_7)$cycloalkyl, bridged $(C_3-C_7)$cycloalkyl and (4-7 membered) heterocycloalkyl; all of which are optionally substituted with one or more substituents independently selected from $R^4$; or pharmaceutically acceptable salts, enantiomers, mixtures of enantiomers, diastereomers, mixtures of diastereomers, hydrates and solvates thereof.

Clause 27. A compound according to clause 26, wherein $R^1$ is 6 membered heteroaryl; and $R^2$ is $(C_3-C_7)$cycloalkyl or bridged $(C_3-C_7)$cycloalkyl both of which are optionally substituted with one of $R^4$; or pharmaceutically acceptable salts, enantiomers, mixtures of enantiomers, diastereomers, mixtures of diastereomers, hydrates and solvates thereof.

Clause 28. A compound according to any one of the clauses 1-20, wherein $R^1$ is 6 membered heteroaryloxy; and $R^2$ is $(C_3-C_7)$cycloalkyl or bridged $(C_3-C_7)$cycloalkyl both of which are optionally substituted with one of $R^4$; or pharmaceutically acceptable salts, enantiomers, mixtures of enantiomers, diastereomers, mixtures of diastereomers, hydrates and solvates thereof.

Clause 29. A compound according to any one of the clauses 1-20, wherein $R^1$ is phenyl optionally substituted with one of halogen or $(C_1-C_4)$alkyl; and $R^2$ is selected from the group consisting of tetrahydropyranyl, piperidinyl, pyrrolidinyl, dioxothietanyl, dioxothianyl and bicyclo[1.1.1]pentyl; all of which are optionally substituted with one of —C(O)(OR$^x$); and R$^x$ is $(C_1-C_4)$alkyl; or pharmaceutically acceptable salts, enantiomers, mixtures of enantiomers, diastereomers, mixtures of diastereomers, hydrates and solvates thereof.

Clause 30. A compound according to any one of the clauses 1-20, wherein $R^1$ is phenoxy; optionally substituted with fluoro; and $R^2$ is selected from the group consisting of tetrahydropyranyl, and piperidinyl substituted with —C(O)(OR$^x$); and R$^x$ is $(C_1-C_4)$alkyl; or pharmaceutically acceptable salts, enantiomers, mixtures of enantiomers, diastereomers, mixtures of diastereomers, hydrates and solvates thereof.

Clause 31. A compound according to any one of the clauses 1-20, wherein $R^1$ is pyridinyl or pyridyloxy; and $R^2$ is selected from the group consisting of cyclobutyl substituted with methyl, and bicyclo[1.1.1]pentyl.

Clause 32. A compound according to any one of the preceding clauses selected from the group consisting of (R)-2-(3-Phenylazetidin-1-yl)-4-((tetrahydro-2H-pyran-4-yl)amino)-6,7-dihydrothieno[3,2-d]pyrimidine 5-oxide, (R)-2-(3-Phenoxyazetidin-1-yl)-4-((tetrahydro-2H-pyran-4-yl)amino)-6,7-dihydrothieno[3,2-d]pyrimidine 5-oxide, (R)-2-(3-(4-Fluorophenoxy)azetidin-1-yl)-4-((tetrahydro-2H-pyran-4-yl)amino)-6,7-dihydrothieno[3,2-d]pyrimidine 5-oxide, (R)-3-((5-Oxido-2-(3-phenylazetidin-1-yl)-6,7-dihydrothieno[3,2-d]pyrimidin-4-yl)amino)thietane 1,1-dioxide, Methyl (3S)-3-(((5R)-5-oxido-2-(3-phenylazetidin-1-yl)-6,7-dihydrothieno[3,2-d]pyrimidin-4-yl)amino)pyrrolidine-1-carboxylate, Methyl (3R)-3-(((5R)-5-Oxido-2-(3-phenylazetidin-1-yl)-6,7-dihydrothieno[3,2-d]pyrimidin-4-yl)amino)pyrrolidine-1-carboxylate, Methyl (3R)-3-(((5R)-2-(3-(4-Fluorophenoxy)azetidin-1-yl)-5-oxido-6,7-dihydrothieno[3,2-d]pyrimidin-4-yl)amino)piperidine-1-carboxylate, Methyl (3S)-3-(((5R)-2-(3-(4-Fluorophenoxy)azetidin-1-yl)-5-oxido-6,7-dihydrothieno[3,2-d]pyrimidin-4-yl)amino)piperidine-1-carboxylate, (R)-4-(Bicyclo[1.1.1]pentan-1-ylamino)-2-(3-(4-fluorophenyl)azetidin-1-yl)-6,7-dihydrothieno[3,2-d]pyrimidine 5-oxide, (R)-4-(Bicyclo[1.1.1]pentan-1-ylamino)-2-(3-(4-fluorophenoxy)azetidin-1-yl)-6,7-dihydrothieno[3,2-d]pyrimidine 5-oxide, (R)-4-(Bicyclo[1.1.1]pentan-1-ylamino)-2-(3-phenylazetidin-1-yl)-6,7-dihydrothieno[3,2-d]pyrimidine 5-oxide,
(R)-4-(Bicyclo[1.1.1]pentan-1-ylamino)-2-(3-(pyridin-2-yl)azetidin-1-yl)-6,7-dihydrothieno[3,2-d]pyrimidine 5-oxide,
(R)-4-(Bicyclo[1.1.1]pentan-1-ylamino)-2-(3-(3-fluorophenyl)azetidin-1-yl)-6,7-dihydrothieno[3,2-d]pyrimidine 5-oxide,
(R)-4-(Bicyclo[1.1.1]pentan-1-ylamino)-2-(3-(pyridin-3-yloxy)azetidin-1-yl)-6,7-dihydrothieno[3,2-d]pyrimidine 5-oxide,
(R)-4-((1-Methylcyclobutyl)amino)-2-(3-(pyridin-2-yl)azetidin-1-yl)-6,7-dihydrothieno[3,2-d]pyrimidine 5-oxide,
(R)-4-((1-Methylcyclobutyl)amino)-2-(3-(pyridin-3-yl)azetidin-1-yl)-6,7-dihydrothieno[3,2-d]pyrimidine 5-oxide,
(5R)—N-(1,1-Dioxothian-4-yl)-5-oxido-2-(3-phenylazetidin-1-yl)-6,7-dihydrothieno[3,2-d]pyrimidin-4-yl-amine,
or a pharmaceutically acceptable salt, enantiomer, mixture of enantiomers, diastereomer, mixture of diastereomers, hydrate and solvate thereof.

Clause 33. A compound which is
(R)-2-(3-Phenylazetidin-1-yl)-4-((tetrahydro-2H-pyran-4-yl)amino)-6,7-dihydrothieno[3,2-d]pyrimidine 5-oxide.

Clause 34. A compound which is
(R)-2-(3-Phenoxyazetidin-1-yl)-4-((tetrahydro-2H-pyran-4-yl)amino)-6,7-dihydrothieno[3,2-d]pyrimidine 5-oxide.

Clause 35. A compound which is
(R)-2-(3-(4-Fluorophenoxy)azetidin-1-yl)-4-((tetrahydro-2H-pyran-4-yl)amino)-6,7-dihydrothieno[3,2-d]pyrimidine 5-oxide.

Clause 36. A compound which is
(R)-3-((5-Oxido-2-(3-phenylazetidin-1-yl)-6,7-dihydrothieno[3,2-d]pyrimidin-4-yl)amino)thietane 1,1-dioxide.

Clause 37. A compound which is
(R)-Methyl (3S)-3-(((5R)-5-oxido-2-(3-phenylazetidin-1-yl)-6,7-dihydrothieno[3,2-d]pyrimidin-4-yl)amino)pyrrolidine-1-carboxylate.

Clause 38. A compound which is
Methyl (3R)-3-(((5R)-5-Oxido-2-(3-phenylazetidin-1-yl)-6,7-dihydrothieno[3,2-d]pyrimidin-4-yl)amino)pyrrolidine-1-carboxylate.

Clause 39. A compound which is
Methyl (3R)-3-(((5R)-2-(3-(4-Fluorophenoxy)azetidin-1-yl)-5-oxido-6,7-dihydrothieno[3,2-d]pyrimidin-4-yl)amino)piperidine-1-carboxylate.

Clause 40. A compound which is
Methyl (3S)-3-(((5R)-2-(3-(4-Fluorophenoxy)azetidin-1-yl)-5-oxido-6,7-dihydrothieno[3,2-d]pyrimidin-4-yl)amino)piperidine-1-carboxylate.

Clause 41. A compound which is
(R)-4-(Bicyclo[1.1.1]pentan-1-ylamino)-2-(3-(4-fluorophenyl)azetidin-1-yl)-6,7-dihydrothieno[3,2-d]pyrimidine 5-oxide.

Clause 42. A compound which is
(R)-4-(Bicyclo[1.1.1]pentan-1-ylamino)-2-(3-(4-fluorophenoxy)azetidin-1-yl)-6,7-dihydrothieno[3,2-d]pyrimidine 5-oxide.

Clause 43. A compound which is
(R)-4-(Bicyclo[1.1.1]pentan-1-ylamino)-2-(3-phenylazetidin-1-yl)-6,7-dihydrothieno[3,2-d]pyrimidine 5-oxide.

Clause 44. A compound which is
(R)-4-(Bicyclo[1.1.1]pentan-1-ylamino)-2-(3-(pyridin-2-yl)azetidin-1-yl)-6,7-dihydrothieno[3,2-d]pyrimidine 5-oxide.

Clause 45. A compound which is
(R)-4-(Bicyclo[1.1.1]pentan-1-ylamino)-2-(3-(3-fluorophenyl)azetidin-1-yl)-6,7-dihydrothieno[3,2-d]pyrimidine 5-oxide.

Clause 46. A compound which is
(R)-4-(Bicyclo[1.1.1]pentan-1-ylamino)-2-(3-(pyridin-3-yloxy)azetidin-1-yl)-6,7-dihydrothieno[3,2-d]pyrimidine 5-oxide.

Clause 47. A compound which is
(R)-4-((1-Methylcyclobutyl)amino)-2-(3-(pyridin-2-yl)azetidin-1-yl)-6,7-dihydrothieno[3,2-d]pyrimidine 5-oxide.

Clause 48. A compound which is
(R)-4-((1-Methylcyclobutyl)amino)-2-(3-(pyridin-3-yl)azetidin-1-yl)-6,7-dihydrothieno[3,2-d]pyrimidine 5-oxide.

Clause 49. A compound which is
(5R)—N-(1,1-Dioxothian-4-yl)-5-oxido-2-(3-phenylazetidin-1-yl)-6,7-dihydrothieno[3,2-d]pyrimidin-4-yl-amine.

Clause 50. A pharmaceutical composition comprising a compound according to any one of clauses 1-49 together with a pharmaceutically acceptable vehicle or excipient or pharmaceutically acceptable carrier(s).

Clause 51. The pharmaceutical composition according to clause 50 further comprising one or more other therapeutically active compound(s).

Clause 52. A use of the compound according to any of the clauses 1-49, for the manufacture of a pharmaceutical composition.

Clause 53. The use of a compound according to clause 52 in the manufacture of a pharmaceutical composition for the treatment or amelioration of a disease, disorder or condition responsive to PDE4 inhibitory activity.

Clause 54 The use according to clause 53, wherein the disease, disorder or condition is dermal diseases, disorders or conditions.

Clause 55. The use according to clause 54, wherein the dermal disease, disorder or condition is proliferative and inflammatory skin disorders, dermatitis, atopic dermatitis, seborrheic dermatitis, contact dermatitis, including irritative contact dermatitis and allergic contact dermatitis, hand dermatitis, psoriasis, psoriasis vulgaris, inverse psoriasis, psoriatic arthritis, spondyloarthritis, epidermal inflammation, alopecia, alopecia areata, rosacea, skin atrophy, steroid induced skin atrophy, photo skin ageing, SAPHO syndrome, (synovitis, acne, pustulosis, hyperostosis and osteitis), acne vulgaris, hidradenitis suppurativa, urticaria, pruritis, and eczema.

Clause 56. The use according to clause 55, wherein the dermal disease, disorder or condition is inflammatory skin disorders.

Clause 57. The use according to clause 55, wherein the dermal disease, disorder or condition is dermatitis, atopic dermatitis, seborrheic dermatitis, contact dermatitis, including irritative contact dermatitis and allergic contact dermatitis or hand dermatitis.

Clause 58. The use according to clause 57, wherein the dermal disease, disorder or condition is atopic dermatitis.

Clause 59. The use according to clause 55, wherein the dermal disease, disorder or condition is psoriasis, psoriasis vulgaris, inverse psoriasis or psoriatic arthritis.

Clause 60. The use according to clause 59, wherein the dermal disease, disorder or condition is psoriasis.

Clause 61. The compound according to any of the clauses 1-49, for use as a medicament.

Clause 62. The compound according to any of the clauses 1-49 for use in the treatment or amelioration of a disease, disorder or condition responsive to PDE4 inhibitory activity.

Clause 63. The compound according to any of the clauses 1-49 for use in the treatment or amelioration of dermal diseases, disorders or conditions.

Clause 64. The compound according to any of the clauses 1-49 for use in the treatment or amelioration of proliferative and inflammatory skin disorders, dermatitis, atopic dermatitis, seborrheic dermatitis, contact dermatitis, including irritative contact dermatitis and allergic contact dermatitis, hand dermatitis, psoriasis, psoriasis vulgaris, inverse psoriasis, psoriatic arthritis, spondyloarthritis, epidermal inflammation, alopecia, alopecia areata, rosacea, skin atrophy, steroid induced skin atrophy, photo skin ageing, SAPHO syndrome, (synovitis, acne, pustulosis, hyperostosis and osteitis), acne vulgaris, hidradenitis suppurativa, urticaria, pruritis, and eczema.

Clause 65. The compound according to any of the clauses 1-49 for use in the treatment or amelioration of inflammatory skin disorders.

Clause 66. The compound according to any of the clauses 1-49 for use in the treatment or amelioration of dermatitis, atopic dermatitis, seborrheic dermatitis, contact dermatitis, including irritative contact dermatitis and allergic contact dermatitis or hand dermatitis.

Clause 67. The compound according to any of the clauses 1-49 for use in the treatment or amelioration of atopic dermatitis.

Clause 68. The compound according to any of the clauses 1-49 for use in the treatment or amelioration of psoriasis, psoriasis vulgaris, inverse psoriasis or psoriatic arthritis.

Clause 69. The compound according to any of the clauses 1-49 for use in the treatment or amelioration of psoriasis.

Clause 70. The compound according to any of the clauses 1-49 for systemic treatment of a disease, disorder or condition responsive to PDE4 inhibitory activity.

Clause 71. The compound according to any of the clauses 1-49 for systemic treatment of dermal diseases, disorders or conditions.

Clause 72. The compound according to any of the clauses 1-49 for systemic treatment of proliferative and inflammatory skin disorders, dermatitis, atopic dermatitis, seborrheic dermatitis, contact dermatitis, including irritative contact dermatitis and allergic contact dermatitis, hand dermatitis, psoriasis, psoriasis vulgaris, inverse psoriasis, psoriatic arthritis, spondyloarthritis, epidermal inflammation, alopecia, alopecia areata, rosacea, skin atrophy, steroid induced skin atrophy, photo skin ageing, SAPHO syndrome, (synovitis, acne, pustulosis, hyperostosis and osteitis), acne vulgaris, hidradenitis suppurativa, urticaria, pruritis, and eczema.

Clause 73. The compound according to any of the clauses 1-49 for systemic treatment of inflammatory skin disorders.

Clause 74. The compound according to any of the clauses 1-49 for systemic treatment of dermatitis, atopic dermatitis, seborrheic dermatitis, contact dermatitis, including irritative contact dermatitis and allergic contact dermatitis or hand dermatitis.

Clause 75. The compound according to any of the clauses 1-49 for systemic treatment of atopic dermatitis.

Clause 76. The compound according to any of the clauses 1-49 for systemic treatment of psoriasis, psoriasis vulgaris, inverse psoriasis or psoriatic arthritis.

Clause 77. The compound according to any of the clauses 1-49 for systemic treatment of psoriasis.

Clause 78. The compound according to any of the clauses 1-49 for oral treatment of a disease, disorder or condition responsive to PDE4 inhibitory activity.

Clause 79. The compound according to any of the clauses 1-49 for oral treatment of dermal diseases, disorders or conditions.

Clause 80. The compound according to any of the clauses 1-49 for oral treatment of proliferative and inflammatory skin disorders, dermatitis, atopic dermatitis, seborrheic dermatitis, contact dermatitis, including irritative contact dermatitis and allergic contact dermatitis, hand dermatitis, psoriasis, psoriasis vulgaris, inverse psoriasis, psoriatic arthritis, spondyloarthritis, epidermal inflammation, alopecia, alopecia areata, rosacea, skin atrophy, steroid induced skin atrophy, photo skin ageing, SAPHO syndrome, (synovitis, acne, pustulosis, hyperostosis and osteitis), acne vulgaris, hidradenitis suppurativa, urticaria, pruritis, and eczema.

Clause 81. The compound according to any of the clauses 1-49 for oral treatment of inflammatory skin disorders.

Clause 82. The compound according to any of the clauses 1-49 for oral treatment of dermatitis, atopic dermatitis, seborrheic dermatitis, contact dermatitis, including irritative contact dermatitis and allergic contact dermatitis or hand dermatitis.

Clause 83. The compound according to any of the clauses 1-49 for oral treatment of atopic dermatitis.

Clause 84. The compound according to any of the clauses 1-49 for oral treatment of psoriasis, psoriasis vulgaris, inverse psoriasis or psoriatic arthritis.

Clause 85. The compound according to any of the clauses 1-49 for oral treatment of psoriasis.

Clause 86. A method for treatment or alleviation of a disease or a disorder or a condition responsive to PDE4 inhibitory activity, which method comprises the step of administering to a living animal body a therapeutically effective amount of a compound according to any of the clauses 1-49.

Clause 87. A method of treating or ameliorating dermal diseases, disorders or conditions, the method comprising administering to a person suffering from at least one of said diseases an effective amount of one or more compounds according to according to any one of clauses 1-49, optionally together with a pharmaceutically acceptable carrier or one or more excipients, optionally in combination with other therapeutically active compounds.

Clause 88. The method according to clause 87, wherein the dermal disease, disorder or condition is selected from the group consisting of proliferative and inflammatory skin disorders, dermatitis, atopic dermatitis, seborrheic dermatitis, contact dermatitis, including irritative contact dermatitis and allergic contact dermatitis, hand dermatitis, psoriasis, psoriasis vulgaris, inverse psoriasis, psoriatic arthritis, spondyloarthritis, epidermal inflammation, alopecia, alopecia areata, rosacea, skin atrophy, steroid induced skin atrophy, photo skin ageing, SAPHO syndrome, (synovitis, acne, pustulosis, hyperostosis and osteitis), acne vulgaris, hidradenitis suppurativa, urticaria, pruritis, and eczema.

Clause 89. The method according to clause 88, wherein the dermal disease, disorder or condition is inflammatory skin disorders.

Clause 90. The method according to clause 88, wherein the dermal disease, disorder or condition is dermatitis, atopic dermatitis, seborrheic dermatitis, contact dermatitis, including irritative contact dermatitis and allergic contact dermatitis or hand dermatitis.

Clause 91. The method according to clause 90, wherein the dermal disease, disorder or condition is atopic dermatitis.

Clause 92. The method according to clause 88, wherein the dermal disease, disorder or condition is psoriasis, psoriasis vulgaris, inverse psoriasis or psoriatic arthritis.

Clause 93. The method according to clause 92, wherein the dermal disease, disorder or condition is psoriasis.

The invention claimed is:

1. A compound of general formula (I)

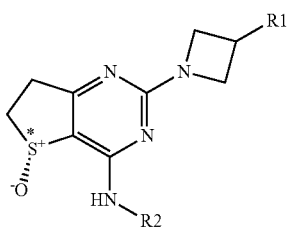

wherein:
- $R^1$ is selected from the group consisting of phenyl, 6-membered heteroaryl, phenoxy, and 6: membered heteroaryloxy; wherein the phenyl, 6-membered heteroaryl, phenoxy, or 6-membered heteroaryloxy is optionally substituted with one or more substituents independently selected from $R^3$;
- $R^2$ is selected from the group consisting of $(C_3-C_7)$ cycloalkyl, bridged $(C_3-C_7)$cycloalkyl, and (4-7 membered) heterocycloalkyl; wherein the $(C_3-C_7)$cycloalkyl, bridged $(C_3-C_7)$cycloalkyl, or (4-7 membered) heterocycloalkyl is optionally substituted with one or more substituents independently selected from $R^4$;
- $R^3$ is selected from the group consisting of fluoro, —CN, $(C_1-C_4)$alkyl, halo$(C_1-C_4)$alkyl, hydroxy$(C_1-C_4)$alkyl, and $(C_3-C_6)$cycloalkyl;
- $R^4$ is selected from the group consisting of fluoro, —CN, —OH, $(C_1-C_4)$alkyl, halo$(C_1-C_4)$alkyl, hydroxy$(C_1-C_4)$alkyl, —OR$^x$, —S(O)$_2$R$^x$, —S(O)$_2$NR$^a$R$^b$, —C(O)R$^x$, —C(O)(OR$^x$), and —C(O)NR$^a$R$^b$;
- R$^x$ is selected from the group consisting of $(C_1-C_4)$alkyl and $(C_3-C_6)$cycloalkyl;
- R$^a$ and R$^b$ are each independently selected from the group consisting of hydrogen, $(C_1-C_4)$alkyl and $(C_3-C_6)$cycloalkyl; and
- S* is a chiral sulfur atom with (R) stereochemistry;
- or a pharmaceutically acceptable salt, enantiomer, mixture of enantiomers, diastereomer, mixture of diastereomers, hydrate or solvate thereof.

2. A compound according to claim 1 wherein $R^1$ is selected from the group consisting of phenyl, pyridinyl, pyridyloxy, and phenoxy; wherein the phenyl, pyridinyl, pyridyloxy, or phenoxy is optionally substituted with one or more substituents independently selected from $R^3$.

3. A compound according to claim 1, wherein $R^2$ is selected from the group consisting of tetrahydropyranyl, piperidinyl, pyrrolidinyl, dioxothietanyl, dioxothianyl, cyclobutyl, and bicyclo[1.1.1]-pentyl; wherein tetrahydropyranyl, piperidinyl, pyrrolidinyl, dioxothietanyl, dioxothianyl, cyclobutyl, or bicyclo[1.1.1]-pentyl is optionally substituted with one or more substituents independently selected from $R^4$.

4. A compound according to claim 1, wherein $R^3$ is fluoro or $(C_1-C_4)$alkyl.

5. A compound according to claim 1, wherein $R^4$ is $(C_1-C_4)$alkyl or —C(O)(OR$^x$); and R$^x$ is $(C_1-C_4)$alkyl.

6. A compound according to any one of the preceding claim 1 selected from the group consisting of:
(i) (R)-2-(3-Phenylazetidin-1-yl)-4-((tetrahydro-2H-pyran-4-yl)amino)-6,7-dihydrothieno[3,2-d]pyrimidine 5-oxide,
(ii) (R)-2-(3-Phenoxyazetidin-1-yl)-4-((tetrahydro-2H-pyran-4-yl)amino)-6,7-dihydrothieno[3,2-d]pyrimidine 5-oxide,
(iii) (R)-2-(3-(4-Fluorophenoxy)azetidin-1-yl)-4-((tetrahydro-2H-pyran-4-yl)amino)-6,7-dihydrothieno[3,2-d]pyrimidine 5-oxide,
(iv) (R)-3-((5-Oxido-2-(3-phenylazetidin-1-yl)-6,7-dihydrothieno[3,2-d]pyrimidin-4-yl)amino)thietane 1,1-dioxide,
(v) Methyl (3S)-3-(((5R)-5-oxido-2-(3-phenylazetidin-1-yl)-6,7-dihydrothieno[3,2-d]pyrimidin-4-yl)amino) pyrrolidine-1-carboxylate,
(vi) Methyl (3R)-3-(((5R)-5-Oxido-2-(3-phenylazetidin-1-yl)-6,7-dihydrothieno[3,2-d]pyrimidin-4-yl)amino) pyrrolidine-1-carboxylate,
(vii) Methyl (3R)-3-(((5R)-2-(3-(4-Fluorophenoxy)azetidin-1-yl)-5-oxido-6,7-dihydrothieno[3,2-d]pyrimidin-4-yl)amino)piperidine-1-carboxylate,
(viii) Methyl (3S)-3-(((5R)-2-(3-(4-Fluorophenoxy)azetidin-1-yl)-5-oxido-6,7-dihydrothieno[3,2-d]pyrimidin-4-yl)amino)piperidine-1-carboxylate,
(ix) (R)-4-(Bicyclo[1.1.1]pentan-1-ylamino)-2-(3-(4-fluorophenyl)azetidin-1-yl)-6,7-dihydrothieno[3,2-d] pyrimidine 5-oxide,
(x) (R)-4-(Bicyclo[1.1.1]pentan-1-ylamino)-2-(3-(4-fluorophenoxy)azetidin-1-yl)-6,7-dihydrothieno[3,2-d]pyrimidine 5-oxide,
(xi) (R)-4-(Bicyclo[1.1.1]pentan-1-ylamino)-2-(3-phenylazetidin-1-yl)-6,7-dihydrothieno[3,2-d]pyrimidine 5-oxide,
(xii) (R)-4-(Bicyclo[1.1.1]pentan-1-ylamino)-2-(3-(pyridin-2-yl)azetidin-1-yl)-6,7-dihydrothieno[3,2-d]pyrimidine 5-oxide,
(xiii) (R)-4-(Bicyclo[1.1.1]pentan-1-ylamino)-2-(3-(3-fluorophenyl)azetidin-1-yl)-6,7-dihydrothieno[3,2-d] pyrimidine 5-oxide,
(xiv) (R)-4-(Bicyclo[1.1.1]pentan-1-ylamino)-2-(3-(pyridin-3-yloxy)azetidin-1-yl)-6,7-dihydrothieno[3,2-d] pyrimidine 5-oxide,
(xv) (R)-4-((1-Methylcyclobutyl)amino)-2-(3-(pyridin-2-yl)azetidin-1-yl)-6,7-dihydrothieno[3,2-d]pyrimidine 5-oxide,
(xvi) (R)-4-((1-Methylcyclobutyl)amino)-2-(3-(pyridin-3-yl)azetidin-1-yl)-6,7-dihydrothieno[3,2-d]pyrimidine 5-oxide, and
(xvii)(5R)—N-(1,1-Dioxothian-4-yl)-5-oxido-2-(3-phenylazetidin-1-yl)-6,7-dihydrothieno[3,2-d]pyrimidin-4-yl-amine, or a pharmaceutically acceptable salt, enantiomer, mixture of enantiomers, diastereomer, mixture of diastereomers, hydrate and solvate thereof.

7. A pharmaceutical composition comprising a compound according to 1 and one or more pharmaceutically acceptable vehicles, excipients, or carriers.

8. A method for treatment or alleviation of a disease or a disorder or a condition responsive to PDE4 inhibitory activity, comprising administering to a subject in need thereof a therapeutically effective amount of a compound according to claim 1.

9. A method of treating or ameliorating one or more dermal diseases, disorders, or conditions, comprising administering to a subject in need thereof a therapeutically effective amount of a compound according to claim 1.

10. The method according to claim 9, wherein the dermal disease, disorder, or condition is selected from the group consisting of proliferative and inflammatory skin disorders, dermatitis, atopic dermatitis, seborrheic dermatitis, contact dermatitis, hand dermatitis, psoriasis, psoriasis vulgaris, inverse psoriasis, psoriatic arthritis, spondyloarthritis, epidermal inflammation, alopecia, alopecia areata, rosacea, skin atrophy, steroid induced skin atrophy, photo skin ageing, SAPHO syndrome, acne vulgaris, hidradenitis suppurativa, urticaria, pruritis, and eczema.

11. A method of treating or ameliorating one or more dermal diseases, disorders, or conditions, comprising administering to a subject in need thereof a therapeutically effective amount of a pharmaceutical composition according to claim 7.

12. The method according to claim 11, wherein the dermal disease, disorder, or condition is selected from the group consisting of proliferative and inflammatory skin disorders, dermatitis, atopic dermatitis, seborrheic dermatitis, contact dermatitis, hand dermatitis, psoriasis, psoriasis vulgaris, inverse psoriasis, psoriatic arthritis, spondyloarthritis, epidermal inflammation, alopecia, alopecia areata, rosacea, skin atrophy, steroid induced skin atrophy, photo skin ageing, SAPHO syndrome, acne vulgaris, hidradenitis suppurativa, urticaria, pruritis, and eczema.

* * * * *